United States Patent
Agar

(10) Patent No.: US 10,983,126 B2
(45) Date of Patent: Apr. 20, 2021

(54) SYSTEM AND METHOD FOR ANALYZING TISSUE FOR THE PRESENCE OF CANCER USING BIO-MARKER PROFILES

(71) Applicants: BRIGHAM AND WOMEN'S HOSPITAL, INC., Boston, MA (US); Nathalie Agar, Newton, MA (US)

(72) Inventor: Nathalie Agar, Newton, MA (US)

(73) Assignee: The Brigham and Women's Hospital, Boston, MA (US)

( * ) Notice: Subject to any disclaimer, the term of this patent is extended or adjusted under 35 U.S.C. 154(b) by 204 days.

(21) Appl. No.: 14/893,830

(22) PCT Filed: Jun. 2, 2014

(86) PCT No.: PCT/US2014/040501
§ 371 (c)(1),
(2) Date: Nov. 24, 2015

(87) PCT Pub. No.: WO2014/204638
PCT Pub. Date: Dec. 24, 2014

(65) Prior Publication Data
US 2016/0178629 A1    Jun. 23, 2016

Related U.S. Application Data

(60) Provisional application No. 61/829,698, filed on May 31, 2013.

(51) Int. Cl.
*G01N 33/574* (2006.01)
*G01N 33/92* (2006.01)
*G01N 33/68* (2006.01)

(52) U.S. Cl.
CPC ... *G01N 33/57415* (2013.01); *G01N 33/6848* (2013.01); *G01N 33/92* (2013.01); *G01N 2405/00* (2013.01); *G01N 2560/00* (2013.01)

(58) Field of Classification Search
CPC ......... G01N 33/57415; G01N 33/6848; G01N 33/92
See application file for complete search history.

(56) References Cited

PUBLICATIONS

Rauser et al. "Classification of HER2 Receptor Status in Breast Cancer Tissues by MALDI Imaging Mass Spectrometry" Journal of Proteome Research 2010, 9, 1854-1863 (Year: 2010).*
The International Search Report and Written Opinion dated Dec. 11, 2014 for International Application No. PCT/US2014/040501.
Eberlin, LS et al., DESI Then MALDI Mass Spectrometry Imaging of Lipid and Protein Distributions in Single Tissue Sections. Analytical Chemistry. Nov. 15, 2011, vol. 83, No. 22, pp. 8366-8371; abstract; p. 3, third paragraph to fourth paragraph; p. 6, first paragraph; figures 1-4. DOI: 10.1021/ac202016x.
New Tool to Help Brain Surgeons One Step Closer to Operating Room [online]. Purdue University. Jan. 9, 2013 [retrieved on Nov. 13, 2014]. Retrieved from the Internet: <URL: http://www.purdue.edu/newsroom/releases/2013/Q1/new-tool-to-help-brain-surgeons-one-step-closer-to-operating-room.html>; pp. 1-4; p. 1, paragraphs 2-3; p. 2, paragraph 9; p. 3, first paragraph to second paragraph; p. 4; figures 1-2.
Reusch, W. Lipids [online]. May 5, 2013 [retrieved on Nov. 13, 2014]. Retrieved from the Internet: <URL: http://www2.chemistry.msu.edu/faculty/reusch/VirTxtJml/lipids.htm>; pp. 1-15; p. 1, first paragraph to fourth paragraph.
Eberlin, LS. Developments in Ambient Mass Spectrometry Imaging and Its Applications in Biomedical Research and Cancer Diagnosis. Purdue University, Aug. 2012 [retrieved on Nov. 13, 2014]. Retrieved from the Internet: <URL: http://search.proquest.com/docview/1221239303>; pp. 1-280, p. 86, first paragraph; figures 3.21, 3.6, 5.9; Table 5.2.
Calligaris, D et al. Application of Desportion Electrospray Ionization Mass Spectrometry Imaging in Breast Cancer Margin Analysis. PNAS. Oct. 21, 2014, vol. 111, No. 42; pp. 15184-15189. www.pnas.org.cgi/doi/10.1073/pnas.1408129111.

* cited by examiner

*Primary Examiner* — Louise W Humphrey
*Assistant Examiner* — Srikanth Patury
(74) *Attorney, Agent, or Firm* — Quarles & Brady LLP

(57) ABSTRACT

A system and method for intra-operative sample analysis including acquiring a tissue sample, preparing the tissue sample for mass spectrometry imaging, conducting a mass spectrometry imaging procedure on the tissue sample to produce an image, and analyzing the image to determine the presence or absence of a bio-marker.

5 Claims, 27 Drawing Sheets

FIG. 1.

Summarized description of samples from 14 research subjects

|  | tumor center | tumor edge | 2cm away | 5cm away | contralateral | Receptor Status | | | Age | Gender |
|---|---|---|---|---|---|---|---|---|---|---|
|  |  |  |  |  |  | ER | PR | Her2 |  |  |
| subject 1 | Y | Y | Y | Y | Y | positive | positive | negative | 42 | female |
| subject 2 | Y | Y | Y | Y | Y | negative | negative | negative | 63 | female |
| subject 3 | Y | Y | Y | Y | N | positive | positive | negative | 65 | male |
| subject 4 | Y | Y | Y | Y | N | positive | positive | negative | 76 | female |
| subject 5 | Y | Y | Y | Y | N | - | - | - | - | - |
| subject 6 | Y | Y | Y | Y | N | positive | positive | positive | 46 | female |
| subject 7 | Y | Y | Y | Y | N | positive | positive | negative | 59 | female |
| subject 8 | Y | Y | Y | Y | N | negative | negative | positive | 60 | female |
| subject 9 | Y | Y | Y | Y | Y | positive | positive | negative | 38 | female |
| subject 10 | Y | Y | Y | Y | N | positive | positive | negative | 48 | female |
| subject 11 | Y | Y | Y | Y | N | negative | negative | negative | 64 | female |
| subject 12 | Y | Y | Y | Y | Y | positive | positive | negative | 47 | female |
| subject 13 | Y | Y | Y | Y | Y | positive | positive | negative | 38 | female |
| subject 14 | Y | Y | Y | Y | N | positive | positive | negative | 40 | female |

FIG. 2.
Detail of m/z 282.24

| LM_ID | COMMON NAME | SYSTEMATIC NAME | FORMULA | CATEGORY | MAIN_CLASS | SUB_CLASS |
|---|---|---|---|---|---|---|
| LMFA01020206 | - | 2-methyl-16-heptadecenoic acid | C18H34O2 | Fatty Acyls [FA] | Fatty Acids and Conjugates [FA01] | Branched fatty acids [FA0102] |
| LMFA01020372 | 17:1(4)(16Me) | 16-methyl-4-heptadecenoic acid | C18H34O2 | Fatty Acyls [FA] | Fatty Acids and Conjugates [FA01] | Branched fatty acids [FA0102] |
| LMFA01020373 | 17:1(6)(9Me) | 9-methyl-6-heptadecenoic acid | C18H34O2 | Fatty Acyls [FA] | Fatty Acids and Conjugates [FA01] | Branched fatty acids [FA0102] |
| LMFA01020374 | 17:1(12)(7Me) | 7-methyl-12-heptadecenoic acid | C18H34O2 | Fatty Acyls [FA] | Fatty Acids and Conjugates [FA01] | Branched fatty acids [FA0102] |
| LMFA01030002 | Oleic acid | 9Z-octadecenoic acid | C18H34O2 | Fatty Acyls [FA] | Fatty Acids and Conjugates [FA01] | Unsaturated fatty acids [FA0103] |
| LMFA01030061 | - | 2Z-octadecenoic acid | C18H34O2 | Fatty Acyls [FA] | Fatty Acids and Conjugates [FA01] | Unsaturated fatty acids [FA0103] |
| LMFA01030062 | trans-2-oleic acid | 2Z-octadecenoic acid | C18H34O2 | Fatty Acyls [FA] | Fatty Acids and Conjugates [FA01] | Unsaturated fatty acids [FA0103] |
| LMFA01030063 | 3-octadecylenic acid | 3-octadecenoic acid | C18H34O2 | Fatty Acyls [FA] | Fatty Acids and Conjugates [FA01] | Unsaturated fatty acids [FA0103] |
| LMFA01030064 | 4-octadecylenic acid | 4-octadecenoic acid | C18H34O2 | Fatty Acyls [FA] | Fatty Acids and Conjugates [FA01] | Unsaturated fatty acids [FA0103] |
| LMFA01030065 | 5E-octadecylenic acid | 5E-octadecenoic acid | C18H34O2 | Fatty Acyls [FA] | Fatty Acids and Conjugates [FA01] | Unsaturated fatty acids [FA0103] |
| LMFA01030066 | 6-octadecylenic acid | 6Z-octadecenoic acid | C18H34O2 | Fatty Acyls [FA] | Fatty Acids and Conjugates [FA01] | Unsaturated fatty acids [FA0103] |
| LMFA01030067 | Petroselaidic acid | 6E-octadecenoic acid | C18H34O2 | Fatty Acyls [FA] | Fatty Acids and Conjugates [FA01] | Unsaturated fatty acids [FA0103] |

FIG. 2 (continued)
Detail of m/z 282.24

| LM_ID | COMMON_NAME | SYSTEMATIC_NAME | FORMULA | CATEGORY | MAIN_CLASS | SUB_CLASS |
|---|---|---|---|---|---|---|
| LMFA01030068 | - | 7Z-octadecenoic acid | C18H34O2 | Fatty Acyls [FA] | Fatty Acids and Conjugates [FA01] | Unsaturated fatty acids [FA0103] |
| LMFA01030069 | - | 7E-octadecenoic acid | C18H34O2 | Fatty Acyls [FA] | Fatty Acids and Conjugates [FA01] | Unsaturated fatty acids [FA0103] |
| LMFA01030070 | cis-8-oleic acid | 8Z-octadecenoic acid | C18H34O2 | Fatty Acyls [FA] | Fatty Acids and Conjugates [FA01] | Unsaturated fatty acids [FA0103] |
| LMFA01030071 | trans-8-elaidic acid | 8E-octadecenoic acid | C18H34O2 | Fatty Acyls [FA] | Fatty Acids and Conjugates [FA01] | Unsaturated fatty acids [FA0103] |
| LMFA01030073 | 9-elaidic acid | 9E-octadecenoic acid | C18H34O2 | Fatty Acyls [FA] | Fatty Acids and Conjugates [FA01] | Unsaturated fatty acids [FA0103] |
| LMFA01030074 | cis-10-oleic acid | 10Z-octadecenoic acid | C18H34O2 | Fatty Acyls [FA] | Fatty Acids and Conjugates [FA01] | Unsaturated fatty acids [FA0103] |
| LMFA01030075 | - | 10E-octadecenoic acid | C18H34O2 | Fatty Acyls [FA] | Fatty Acids and Conjugates [FA01] | Unsaturated fatty acids [FA0103] |
| LMFA01030076 | cis-vaccenic acid | 11Z-octadecenoic acid | C18H34O2 | Fatty Acyls [FA] | Fatty Acids and Conjugates [FA01] | Unsaturated fatty acids [FA0103] |
| LMFA01030077 | trans-vaccenic acid | 11E-octadecenoic acid | C18H34O2 | Fatty Acyls [FA] | Fatty Acids and Conjugates [FA01] | Unsaturated fatty acids [FA0103] |
| LMFA01030078 | cis-12-oleic acid | 12Z-octadecenoic acid | C18H34O2 | Fatty Acyls [FA] | Fatty Acids and Conjugates [FA01] | Unsaturated fatty acids [FA0103] |
| LMFA01030079 | trans-12-elaidic acid | 12E-octadecenoic acid | C18H34O2 | Fatty Acyls [FA] | Fatty Acids and Conjugates [FA01] | Unsaturated fatty acids [FA0103] |
| LMFA01030080 | - | 15E-octadecenoic acid | C18H34O2 | Fatty Acyls [FA] | Fatty Acids and Conjugates [FA01] | Unsaturated fatty acids [FA0103] |

FIG. 2 (continued)
Detail of m/z 282.24

| LM_ID | COMMON NAME | SYSTEMATIC NAME | FORMULA | CATEGORY | MAIN CLASS | SUB_CLASS |
|---|---|---|---|---|---|---|
| LMFA01030081 | | 16E-octadecenoic acid | C18H34O2 | Fatty Acyls [FA] | Fatty Acids and Conjugates [FA01] | Unsaturated fatty acids [FA0103] |
| LMFA01030290 | | 13Z-octadecenoic acid | C18H34O2 | Fatty Acyls [FA] | Fatty Acids and Conjugates [FA01] | Unsaturated fatty acids [FA0103] |
| LMFA01030291 | | 15Z-octadecenoic acid | C18H34O2 | Fatty Acyls [FA] | Fatty Acids and Conjugates [FA01] | Unsaturated fatty acids [FA0103] |
| LMFA01030292 | | 16Z-octadecenoic acid | C18H34O2 | Fatty Acyls [FA] | Fatty Acids and Conjugates [FA01] | Unsaturated fatty acids [FA0103] |
| LMFA01030293 | | 17-octadecenoic acid | C18H34O2 | Fatty Acyls [FA] | Fatty Acids and Conjugates [FA01] | Unsaturated fatty acids [FA0103] |
| LMFA01030294 | | 3Z-octadecenoic acid | C18H34O2 | Fatty Acyls [FA] | Fatty Acids and Conjugates [FA01] | Unsaturated fatty acids [FA0103] |
| LMFA01030295 | | 4Z-octadecenoic acid | C18H34O2 | Fatty Acyls [FA] | Fatty Acids and Conjugates [FA01] | Unsaturated fatty acids [FA0103] |
| LMFA01030296 | | 5Z-octadecenoic acid | C18H34O2 | Fatty Acyls [FA] | Fatty Acids and Conjugates [FA01] | Unsaturated fatty acids [FA0103] |
| LMFA01030880 | 18:1(13E) | 13E-octadecenoic acid | C18H34O2 | Fatty Acyls [FA] | Fatty Acids and Conjugates [FA01] | Unsaturated fatty acids [FA0103] |
| LMFA01030881 | 18:1(14E) | 14E-octadecenoic acid | C18H34O2 | Fatty Acyls [FA] | Fatty Acids and Conjugates [FA01] | Unsaturated fatty acids [FA0103] |
| LMFA01030882 | 18:1(14Z) | 14Z-octadecenoic acid | C18H34O2 | Fatty Acyls [FA] | Fatty Acids and Conjugates [FA01] | Unsaturated fatty acids [FA0103] |
| LMFA01030895 | 17:1(4)(15 15-methyl-4-heptadecenoic acid | | C18H34O2 | Fatty Acyls [FA] | Fatty Acids and Conjugates [FA01] | Unsaturated fatty acids [FA0103] |

FIG. 3
Detail of m/z 304.24

| LM_ID | COMMON_NAME | SYSTEMATIC_NAME | FORMULA | CATEGORY | MAIN_CLASS | SUB_CLASS |
|---|---|---|---|---|---|---|
| LMFA01020222 | - | 18-methyl-5Z,8Z,11Z,14Z-nonadecatetraenoic acid | C20H32O2 | Fatty Acyls [FA] | Fatty Acids and Conjugates [FA01] | Branched fatty acids [FA0102] |
| LMFA01020367 | 16:3(2E,10E,12E)(3 Me,5Me[R],7My,15 Me) | 3,5R,15-trimethyl-7-methylene-2E,10E,12E-hexadecatrienoic acid | C20H32O2 | Fatty Acyls [FA] | Fatty Acids and Conjugates [FA01] | Branched fatty acids [FA0102] |
| LMFA01020381 | 17:4(2E,4E,9E,11E)(8 8Me[R],10Me,15Me[ R]) | (8R,10,15R-trimethyl-2E,4E,9E,11E-heptadecatetraenoic acid | C20H32O2 | Fatty Acyls [FA] | Fatty Acids and Conjugates [FA01] | Branched fatty acids [FA0102] |
| LMFA01030001 | Arachidonic acid | 5Z,8Z,11Z,14Z-eicosatetraenoic acid | C20H32O2 | Fatty Acyls [FA] | Fatty Acids and Conjugates [FA01] | Unsaturated fatty acids [FA0103] |
| LMFA01030173 | - | 4,8,12,16-eicosatetraenoic acid | C20H32O2 | Fatty Acyls [FA] | Fatty Acids and Conjugates [FA01] | Unsaturated fatty acids [FA0103] |
| LMFA01030175 | - | 6,10,14,18-eicosatetraenoic acid | C20H32O2 | Fatty Acyls [FA] | Fatty Acids and Conjugates [FA01] | Unsaturated fatty acids [FA0103] |
| LMFA01030176 | - | 8,11,14,17-eicosatetraenoic acid | C20H32O2 | Fatty Acyls [FA] | Fatty Acids and Conjugates [FA01] | Unsaturated fatty acids [FA0103] |
| LMFA01030389 | - | 4,7,10,13-Eicosatetraenoic acid | C20H32O2 | Fatty Acyls [FA] | Fatty Acids and Conjugates [FA01] | Unsaturated fatty acids [FA0103] |
| LMFA01030390 | - | 4Z,7Z,10Z,13Z-eicosatetraenoic acid | C20H32O2 | Fatty Acyls [FA] | Fatty Acids and Conjugates [FA01] | Unsaturated fatty acids [FA0103] |
| LMFA01030391 | - | 4Z,8Z,11Z,14Z-eicosatetraenoic acid | C20H32O2 | Fatty Acyls [FA] | Fatty Acids and Conjugates [FA01] | Unsaturated fatty acids [FA0103] |
| LMFA01030392 | - | 5,11,14,17-Eicosatetraenoic acid | C20H32O2 | Fatty Acyls [FA] | Fatty Acids and Conjugates [FA01] | Unsaturated fatty acids [FA0103] |

FIG. 3 (continued)
Detail of m/z 304.24

| LM_ID | COMMON NAME | SYSTEMATIC_NAME | FORMULA | CATEGORY | MAIN_CLASS | SUB_CLASS |
|---|---|---|---|---|---|---|
| LMFA01030393 | - | 5,8,11,14-eicosatetraenoic acid | C20H32O2 | Fatty Acyls [FA] | Fatty Acids and Conjugates [FA01] | Unsaturated fatty acids [FA0103] |
| LMFA01030394 | Juniperonic acid | 5Z,11Z,14Z,17Z-eicosatetraenoic acid | C20H32O2 | Fatty Acyls [FA] | Fatty Acids and Conjugates [FA01] | Unsaturated fatty acids [FA0103] |
| LMFA01030395 | - | 8Z,11Z,14Z,18Z-eicosatetraenoic acid | C20H32O2 | Fatty Acyls [FA] | Fatty Acids and Conjugates [FA01] | Unsaturated fatty acids [FA0103] |
| LMFA01030687 | - | 7,13-Eicosadiynoic acid | C20H32O2 | Fatty Acyls [FA] | Fatty Acids and Conjugates [FA01] | Unsaturated fatty acids [FA0103] |
| LMFA01030688 | - | 8,11-Eicosadiynoic acid | C20H32O2 | Fatty Acyls [FA] | Fatty Acids and Conjugates [FA01] | Unsaturated fatty acids [FA0103] |
| LMFA01030689 | - | 10,13-Eicosadiynoic acid | C20H32O2 | Fatty Acyls [FA] | Fatty Acids and Conjugates [FA01] | Unsaturated fatty acids [FA0103] |
| LMFA01030816 | - | 2E,8Z,11Z,14Z-Eicosatetraenoic acid | C20H32O2 | Fatty Acyls [FA] | Fatty Acids and Conjugates [FA01] | Unsaturated fatty acids [FA0103] |
| LMFA01030817 | 5(E)-Arachidonic acid | 5E,8Z,11Z,14Z-Eicosatetraenoic acid | C20H32O2 | Fatty Acyls [FA] | Fatty Acids and Conjugates [FA01] | Unsaturated fatty acids [FA0103] |

FIG. 3 (continued)
Detail of m/z 304.24

| LM_ID | COMMON_NAME | SYSTEMATIC_NAME | FORMULA | CATEGORY | MAIN_CLASS | SUB_CLASS |
|---|---|---|---|---|---|---|
| LMFA01030818 | omega-3-Arachidonic acid | 8Z,11Z,14Z,17Z-eicosatetraenoic acid | C20H32O2 | Fatty Acyls [FA] | Fatty Acids and Conjugates [FA01] | Unsaturated fatty acids [FA0103] |
| LMFA01030871 | | 20:4(5Z,13Z,16Z,1 9Z) 5Z,13Z,16Z,19Z-eicosatetraenoic acid | C20H32O2 | Fatty Acyls [FA] | Fatty Acids and Conjugates [FA01] | Unsaturated fatty acids [FA0103] |
| LMFA01030905 | | 17:4(2E,4E,9E,11 E)(7Me[R],10Me,1 3Me[S]) 7R,10,13S-trimethyl-2E,4E,9E,11E-heptadecatetraenoic acid | C20H32O2 | Fatty Acyls [FA] | Fatty Acids and Conjugates [FA01] | Unsaturated fatty acids [FA0103] |
| LMFA01030906 | | 16:3(2E,9E,11E)(3 3,5S,15-trimethyl-7-methylene-Me,5Me[S],7My,15 2E,9E,11E-hexadecatrienoic Me) acid | C20H32O2 | Fatty Acyls [FA] | Fatty Acids and Conjugates [FA01] | Unsaturated fatty acids [FA0103] |
| LMFA01140006 | - | 8-[3]-ladderane-octanoic acid | C20H32O2 | Fatty Acyls [FA] | Fatty Acids and Conjugates [FA01] | Carbocyclic fatty acids [FA0114] |
| LMST02020012 | Methandriol | 17alpha-methyl-5-androstene-3beta,17beta-diol | C20H32O2 | Sterol Lipids [ST] | Steroids [ST02] | C19 steroids (androgens) and derivatives [ST0202] |
| LMST02020027 | Mestanolone | 17beta-hydroxy-17-methyl-androstan-3-one | C20H32O2 | Sterol Lipids [ST] | Steroids [ST02] | C19 steroids (androgens) and derivatives [ST0202] |

FIG. 4
Detail of m/z 366.35

| LM_ID | COMMON_NAME | SYSTEMATIC_NAME | FORMULA | CATEGORY | MAIN_CLASS | SUB_CLASS |
|---|---|---|---|---|---|---|
| LMFA01030092 | Nervonic acid | 15Z-tetracosenoic acid | $C_{24}H_{46}O_2$ | Fatty Acyls [FA] | Fatty Acids and Conjugates [FA01] | Unsaturated fatty acids [FA0103] |
| LMFA01030093 | trans-selacholeic acid | 15E-tetracosenoic acid | $C_{24}H_{46}O_2$ | Fatty Acyls [FA] | Fatty Acids and Conjugates [FA01] | Unsaturated fatty acids [FA0103] |
| LMFA07010404 | - | 11-Docosenyl acetate | $C_{24}H_{46}O_2$ | Fatty Acyls [FA] | Fatty esters [FA07] | Wax monoesters [FA0701] |
| LMFA07010659 | 4-Methyl-3-heptyl palmitoleate | 4-Methyl-3-heptyl 9Z-hexadecenoate | $C_{24}H_{46}O_2$ | Fatty Acyls [FA] | Fatty esters [FA07] | Wax monoesters [FA0701] |
| LMFA07040060 | - | 24-Tetracosanolide | $C_{24}H_{46}O_2$ | Fatty Acyls [FA] | Fatty esters [FA07] | Lactones [FA0704] |

FIG. 5
Detail of m/z 392.37

| LM_ID | COMMON_NAME | SYSTEMATIC_NAME | FORMULA | CATEGORY | MAIN CLASS | SUB_CLASS |
|---|---|---|---|---|---|---|
| LMFA01020357 | 25:2(5Z,9Z)(24Me) | 25:2(5Z,9Z)(24-methyl-5Z,9Z-pentacosadienoic acid | C26H48O2 | Fatty Acyls [FA] | Fatty Acids and Conjugates [FA01] | Branched fatty acids [FA0102] |
| LMFA01020358 | 25:2(5Z,9Z)(23Me) | 25:2(5Z,9Z)(23-methyl-5Z,9Z-pentacosadienoic acid | C26H48O2 | Fatty Acyls [FA] | Fatty Acids and Conjugates [FA01] | Branched fatty acids [FA0102] |
| LMFA01030133 | - | 17,20-hexacosadienoic acid | C26H48O2 | Fatty Acyls [FA] | Fatty Acids and Conjugates [FA01] | Unsaturated fatty acids [FA0103] |
| LMFA01030424 | - | 5,9-hexacosadienoic acid | C26H48O2 | Fatty Acyls [FA] | Fatty Acids and Conjugates [FA01] | Unsaturated fatty acids [FA0103] |
| LMFA01030425 | - | 5Z,9Z-hexacosadienoic acid | C26H48O2 | Fatty Acyls [FA] | Fatty Acids and Conjugates [FA01] | Unsaturated fatty acids [FA0103] |
| LMFA01030876 | 26:2(9Z,19Z) | 9Z,19Z-hexacosadienoic acid | C26H48O2 | Fatty Acyls [FA] | Fatty Acids and Conjugates [FA01] | Unsaturated fatty acids [FA0103] |
| LMFA07010656 | 4-Methyl-3-heptyl linoleate | 4-Methyl-3-heptyl 9Z,12Z-octadecadienoate | C26H48O2 | Fatty Acyls [FA] | Fatty esters [FA07] | Wax monoesters [FA0701] |

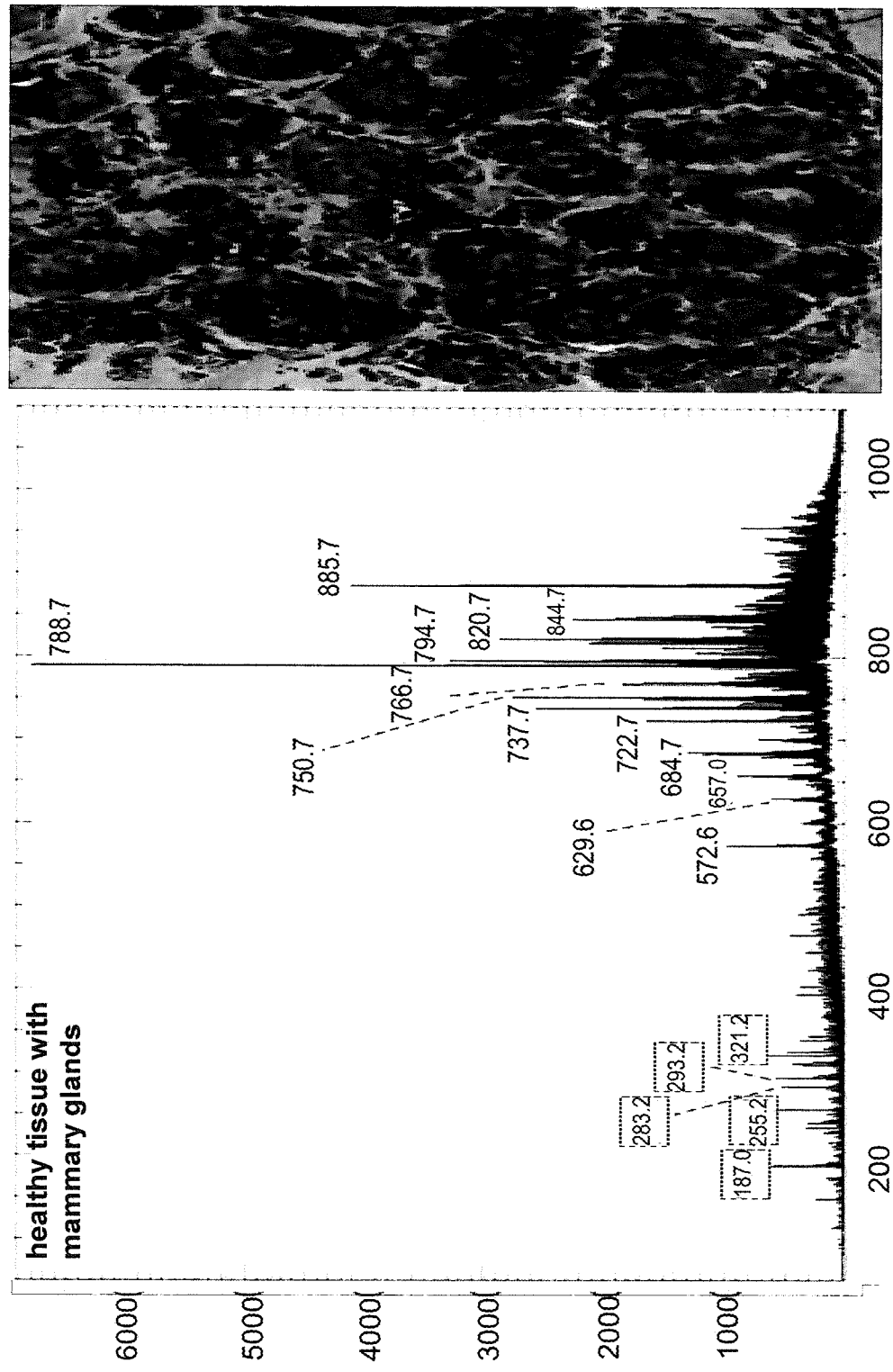
FIGS. 6(a-c) Profiled spectra in negative ion mode using DESI mass spectrometry from a) healthy tissue with mammary glands; b) healthy fatty tissue; c) tumor tissue. The histological images of representative tissue regions are shown on the right under 40X magnification.

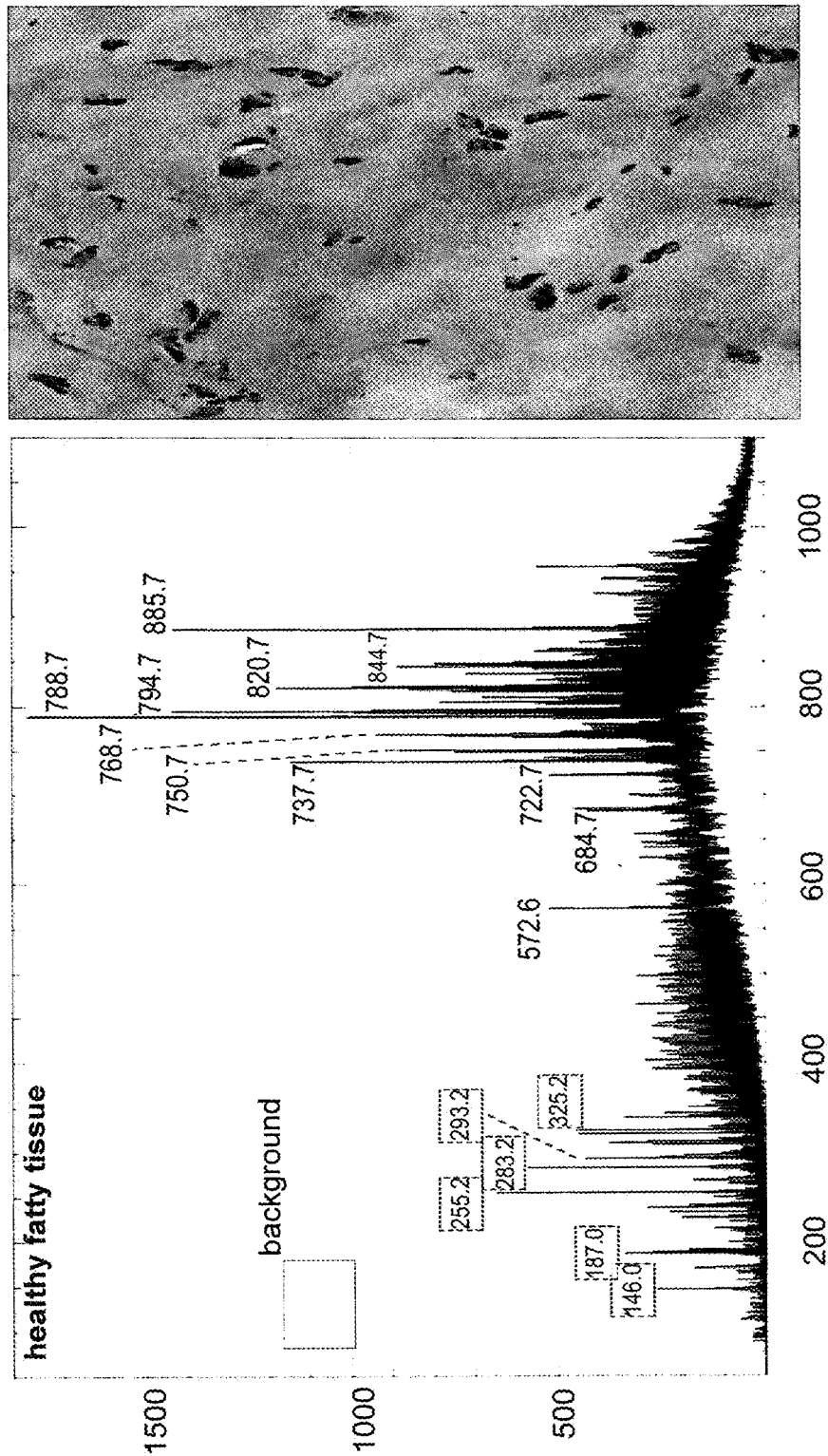
FIGS. 6(a-c) (continued) - Profiled spectra in negative ion mode using DESI mass spectrometry from a) healthy tissue with mammary glands; b) healthy fatty tissue; c) tumor tissue. The histological images of representative tissue regions are shown on the right under 40X magnification.

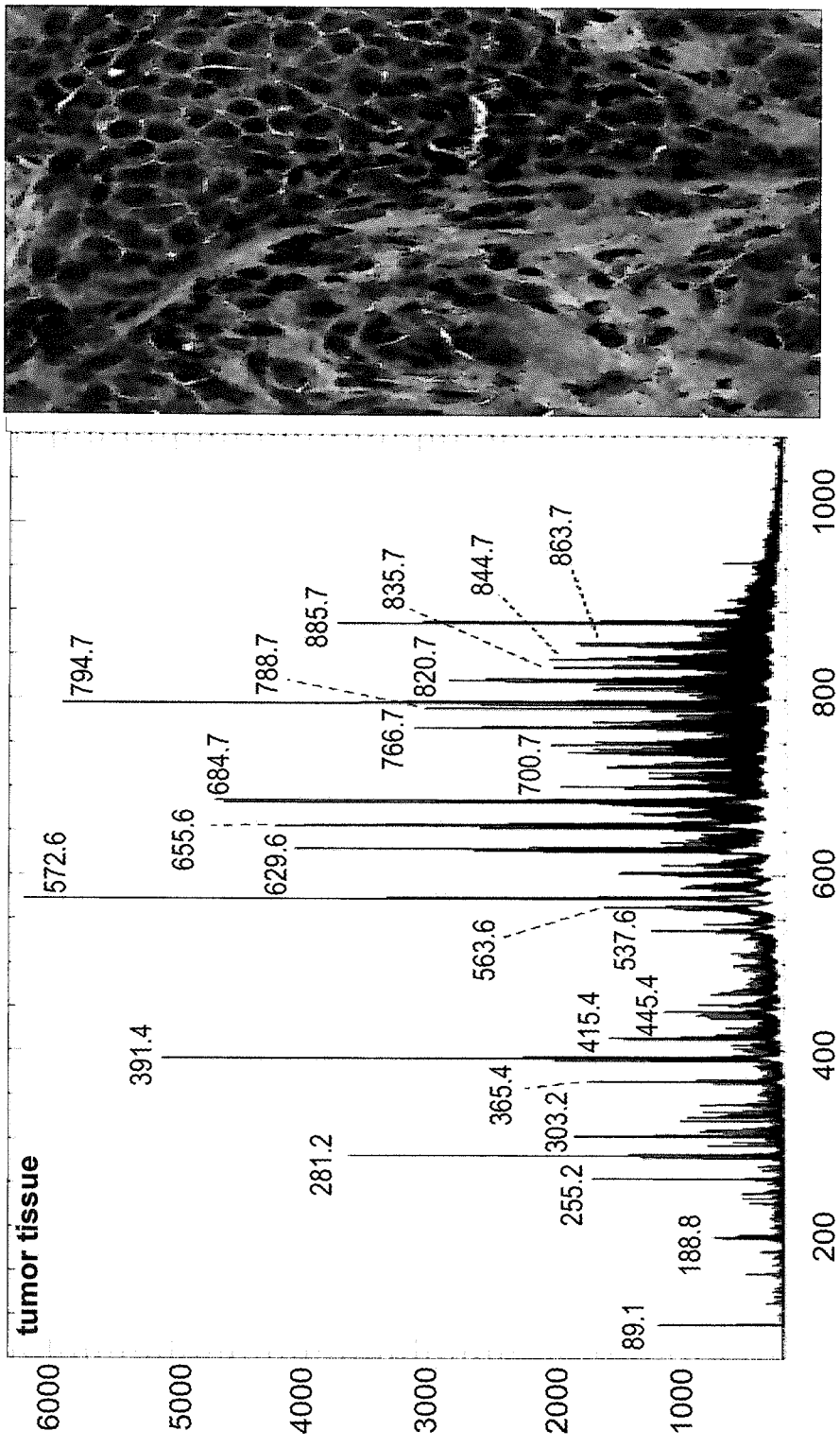
FIGS. 6(a-c) (continued) - Profiled spectra in negative ion mode using DESI mass spectrometry from a) healthy tissue with mammary glands; b) healthy fatty tissue; c) tumor tissue. The histological images of representative tissue regions are shown on the right under 40X magnification.

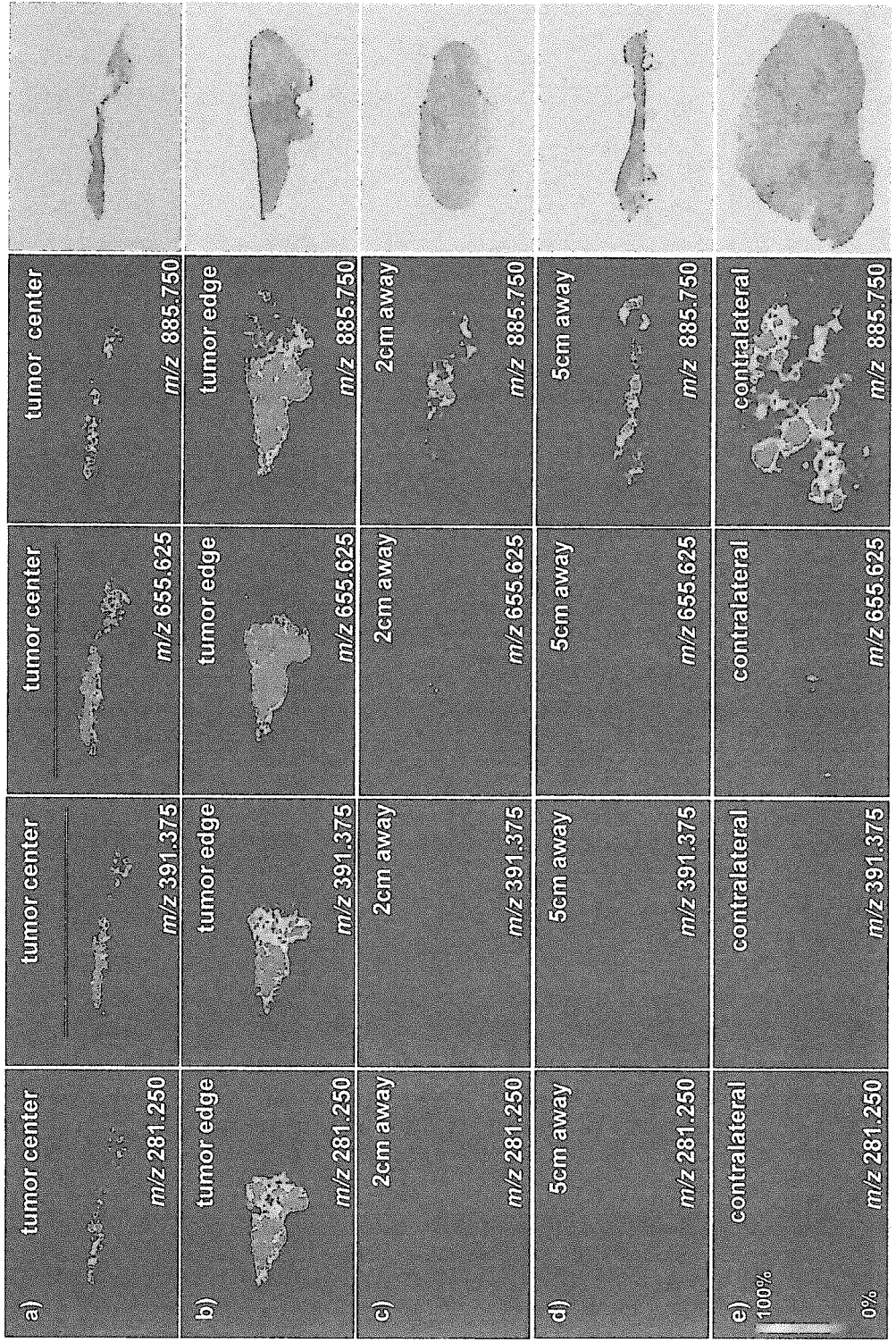
FIGS. 7(a-e) DESI MS images from a) tumor center; b) tumor edge; c) 2cm away; d) 5cm away from tumor; e) contralateral side from research subject #9 showing the distributions of m/z 281.25, m/z 391.375, m/z 655.625 and m/z 885.750. The histological images of the same tissue sections are shown on the right.

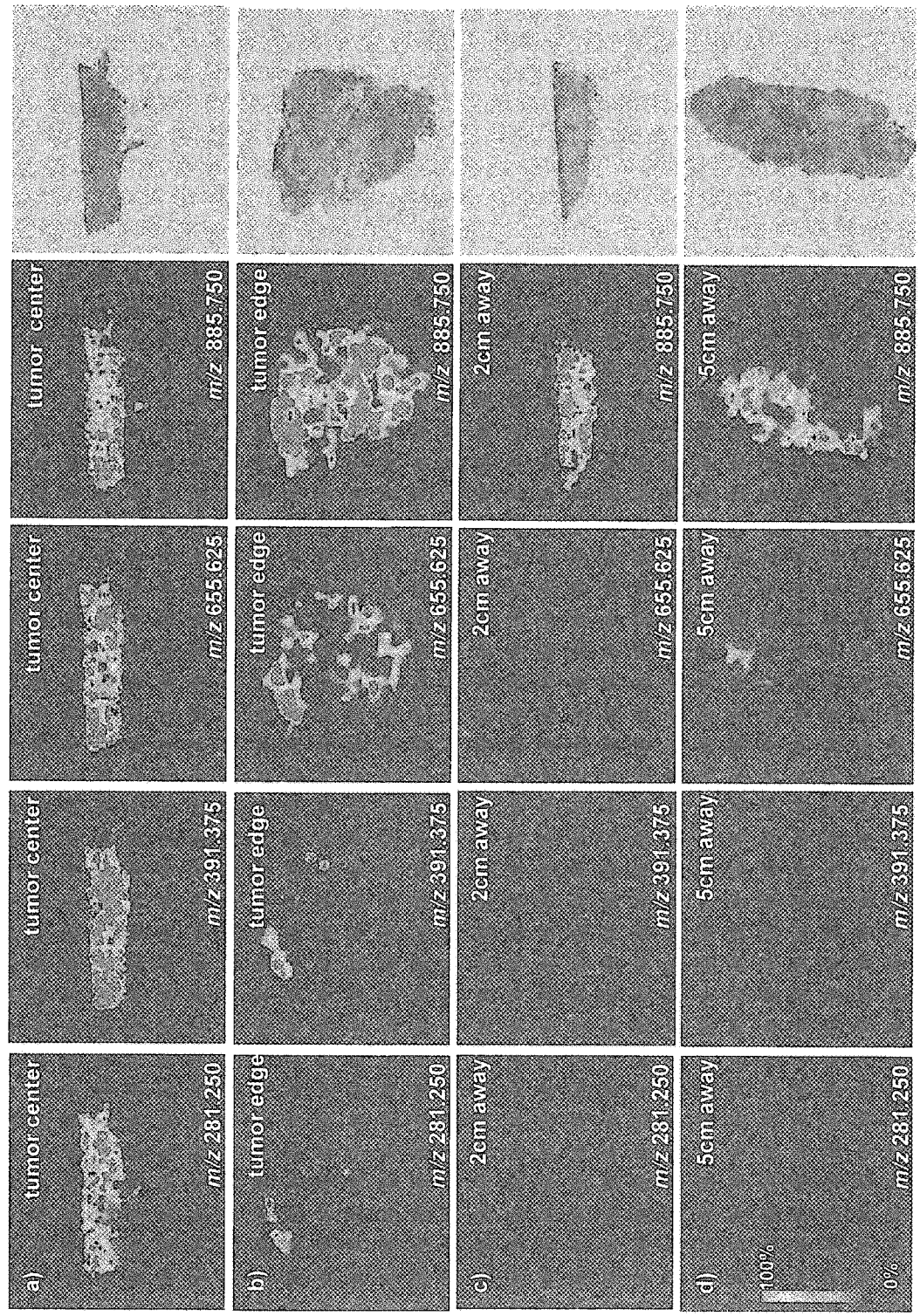
FIGS. 8(a-d) DESI MS images from a) tumor center; b) tumor edge; c) 2cm away; d) 5cm away from tumor from research subject #14 showing the distributions of m/z 281.25, m/z 391.375, m/z 655.625 and m/z 885.750. The histological images of the same tissue sections are shown on the right.

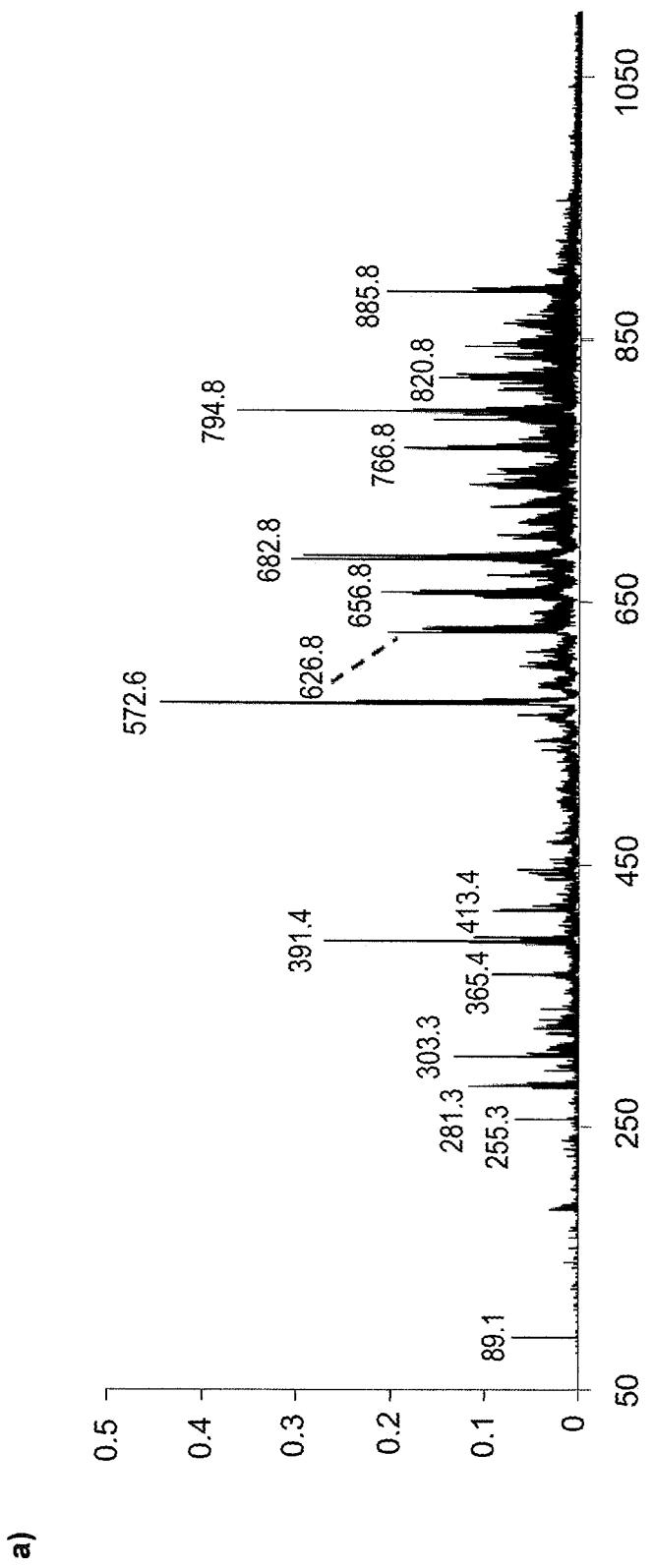
FIGS. 9(a-c) a) Average of 13 normalized spectra from DESI MA analysis of tumor tissue; b) average of 14 normalized spectra from DESI MS analysis of normal tissue; c) the spectrum with b) subtracted from a).

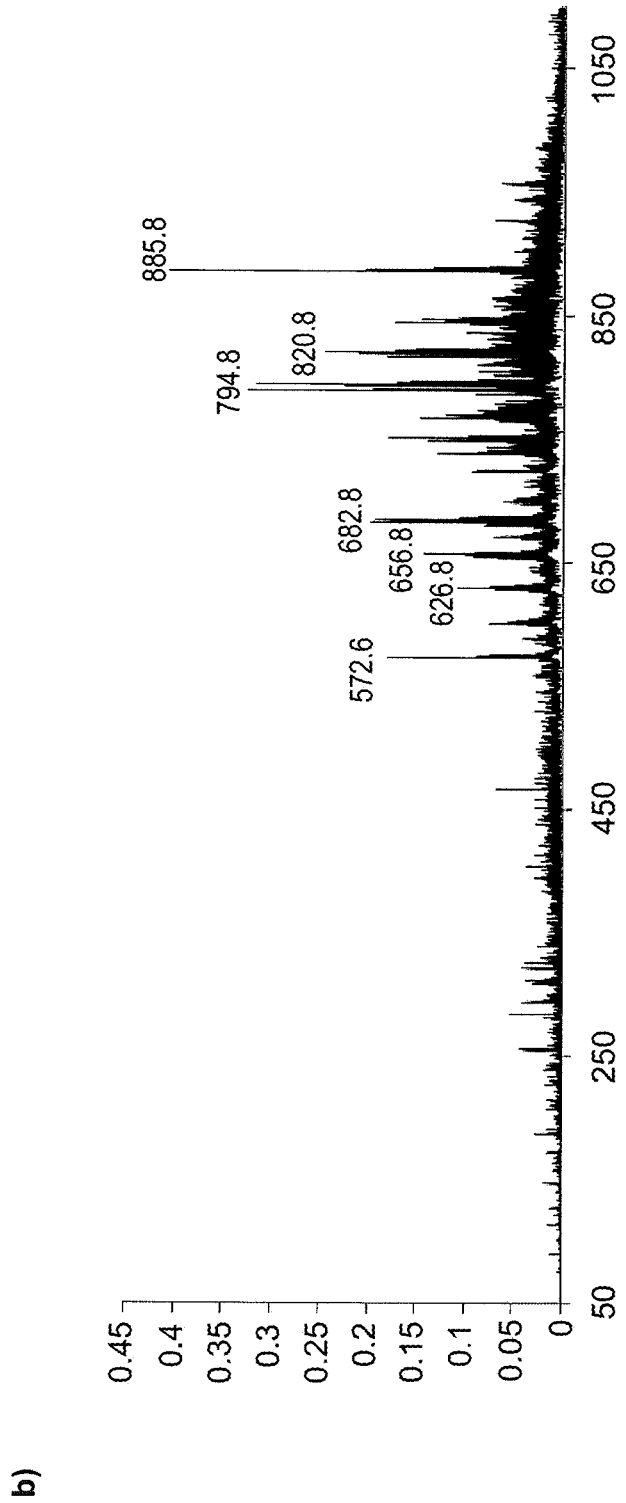
FIGS. 9(a-c) (continued) - a) Average of 13 normalized spectra from DESI MA analysis of tumor tissue; b) average of 14 normalized spectra from DESI MS analysis of normal tissue; c) the spectrum with b) subtracted from a).

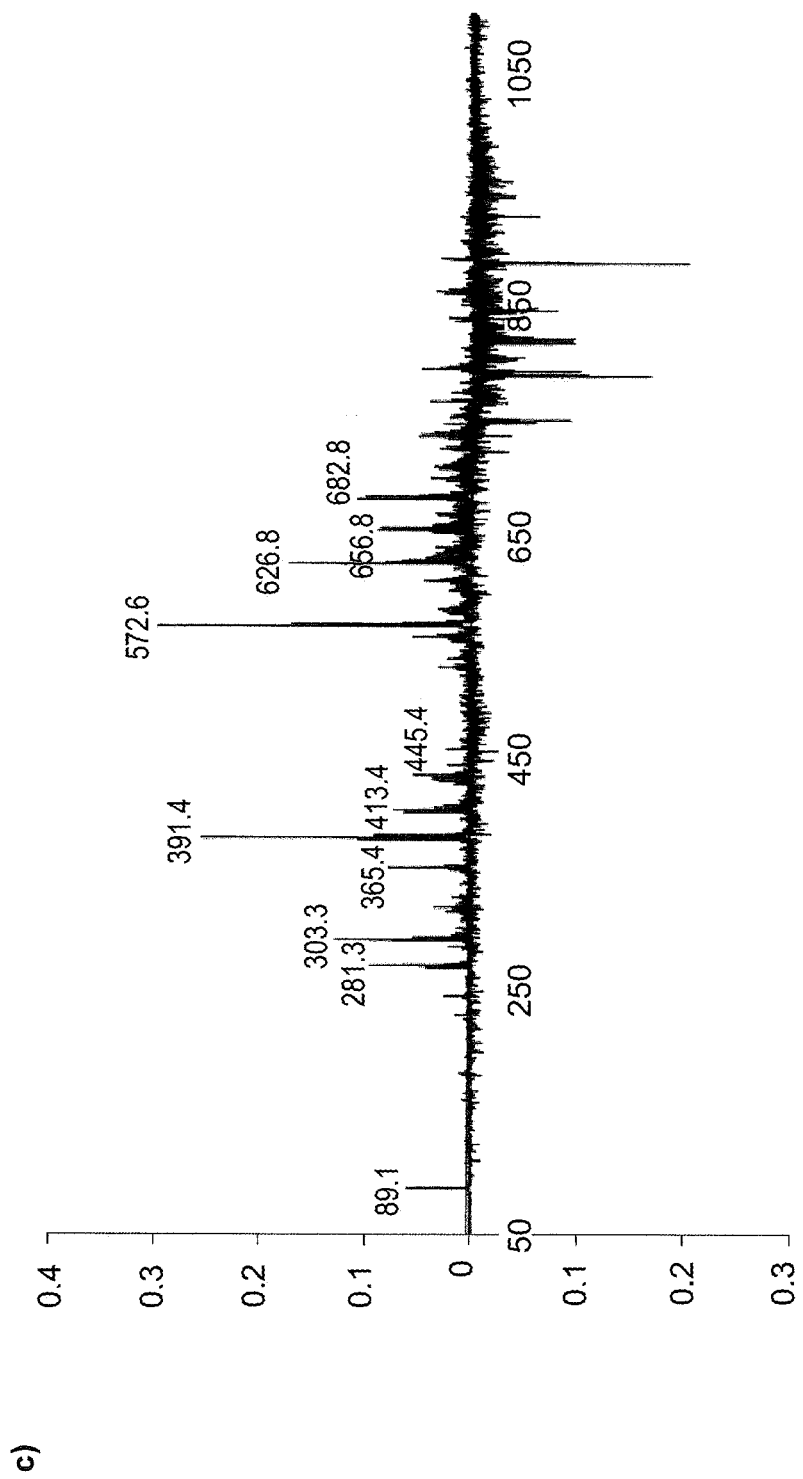
FIGS. 9(a-c) (continued) – a) Average of 13 normalized spectra from DESI MA analysis of tumor tissue; b) average of 14 normalized spectra from DESI MS analysis of normal tissue; c) the spectrum with b) subtracted from a).

a)
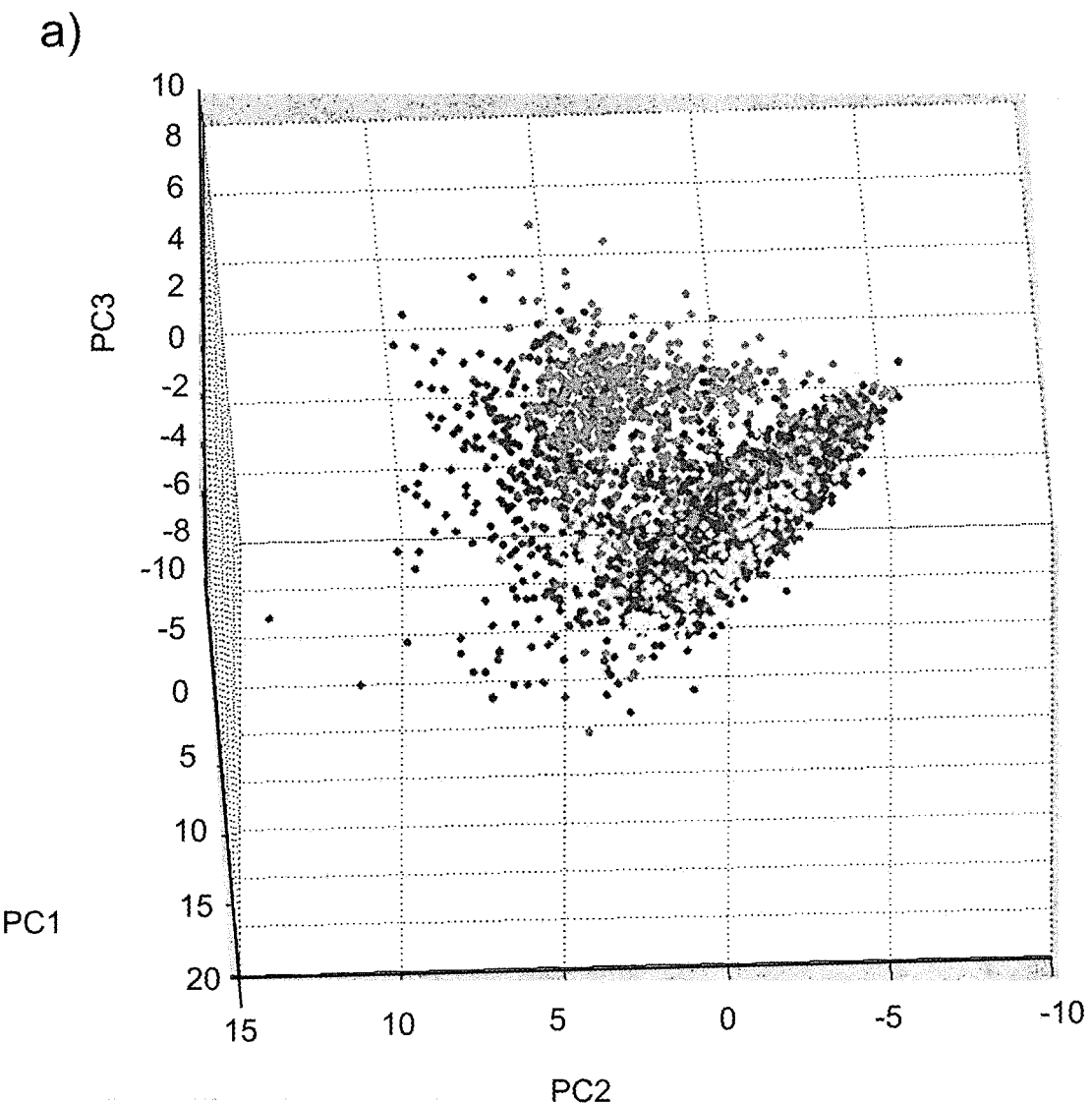
FIGS. 10(a-b)
Case 9
red: center
green: edge
blue: +2cm
yellow: +5 cm
purple: contralateral b)
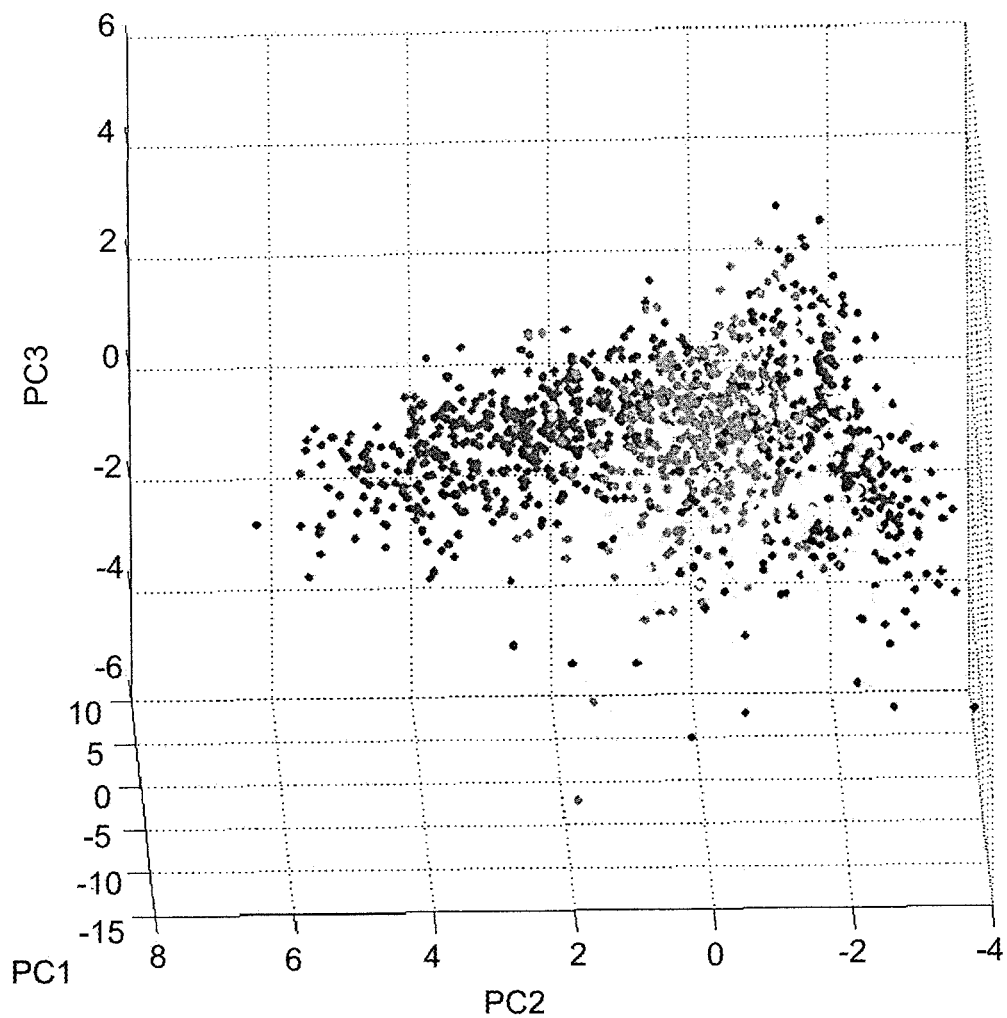
FIGS. 10(a-b) (continued)
Case 14
red: center
green: edge
blue: +2cm
yellow: +5 cm

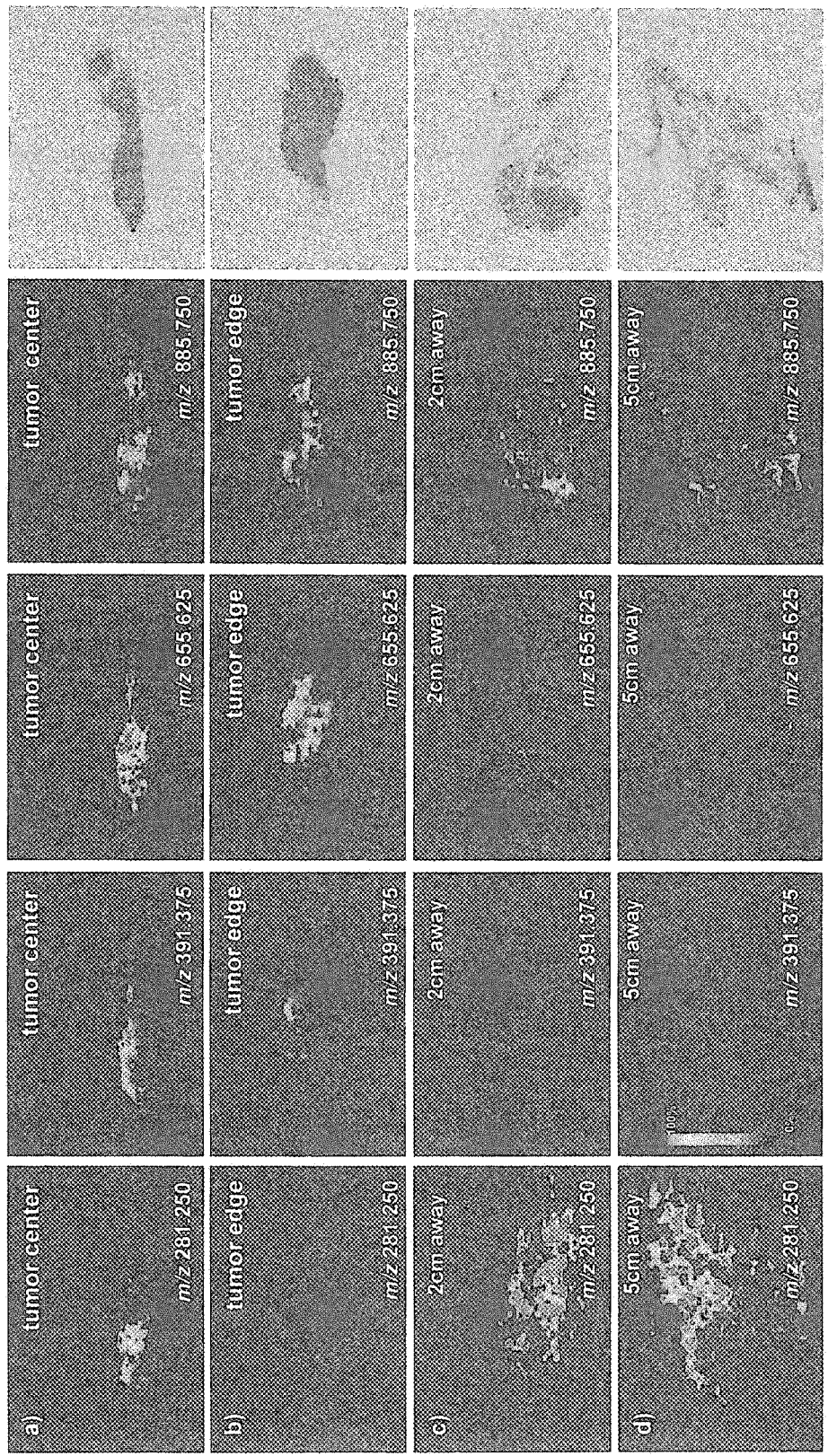
FIGS. 11(a-e) DESI MS images from a) tumor center; b) tumor edge; c) 2cm away ;d) 5cm away from tumor from research subject #5 showing the distributions of m/z 281.25, m/z 391.375, m/z 655.625 and m/z 885.750. The histological images of the same tissue sections are shown on the right. e) the profiled spectrum from the normal tissue in c).

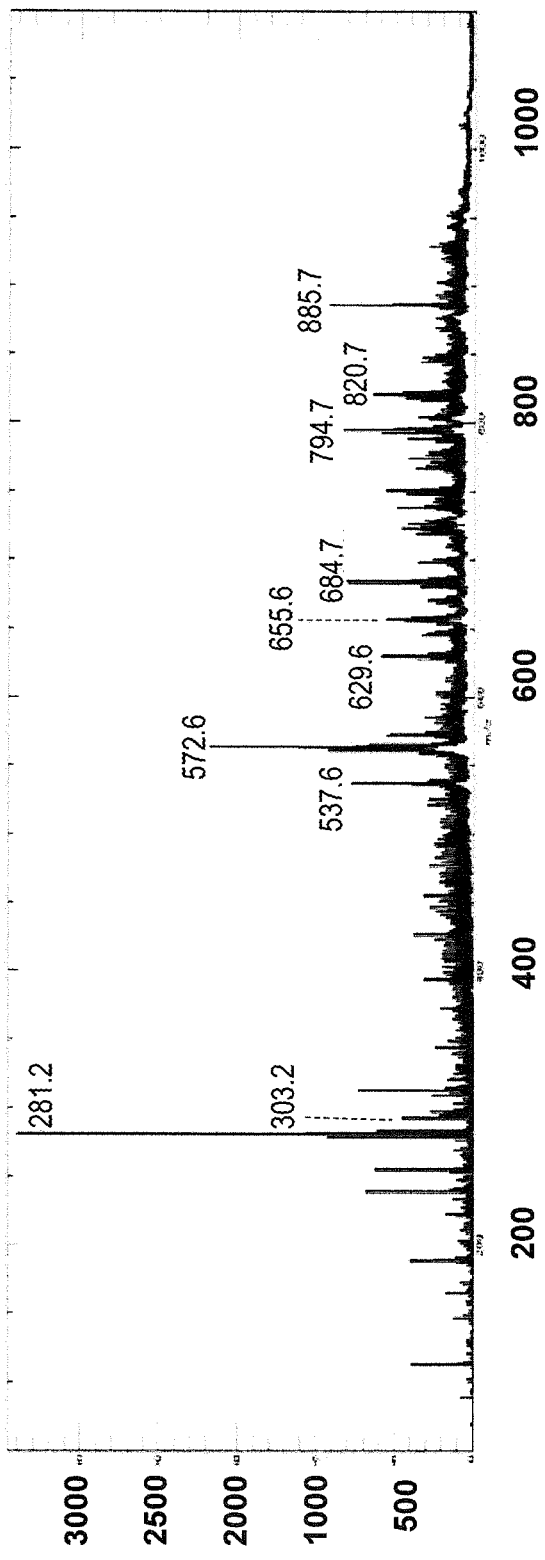
FIGS. 11(a-e) (continued) – DESI MS images from a) tumor center; b) tumor edge; c) 2cm away ;d) 5cm away from tumor from research subject #5 showing the distributions of m/z 281.25, m/z 391.375, m/z 655.625 and m/z 885.750. The histological images of the same tissue sections are shown on the right. e) the profiled spectrum from the normal tissue in c).

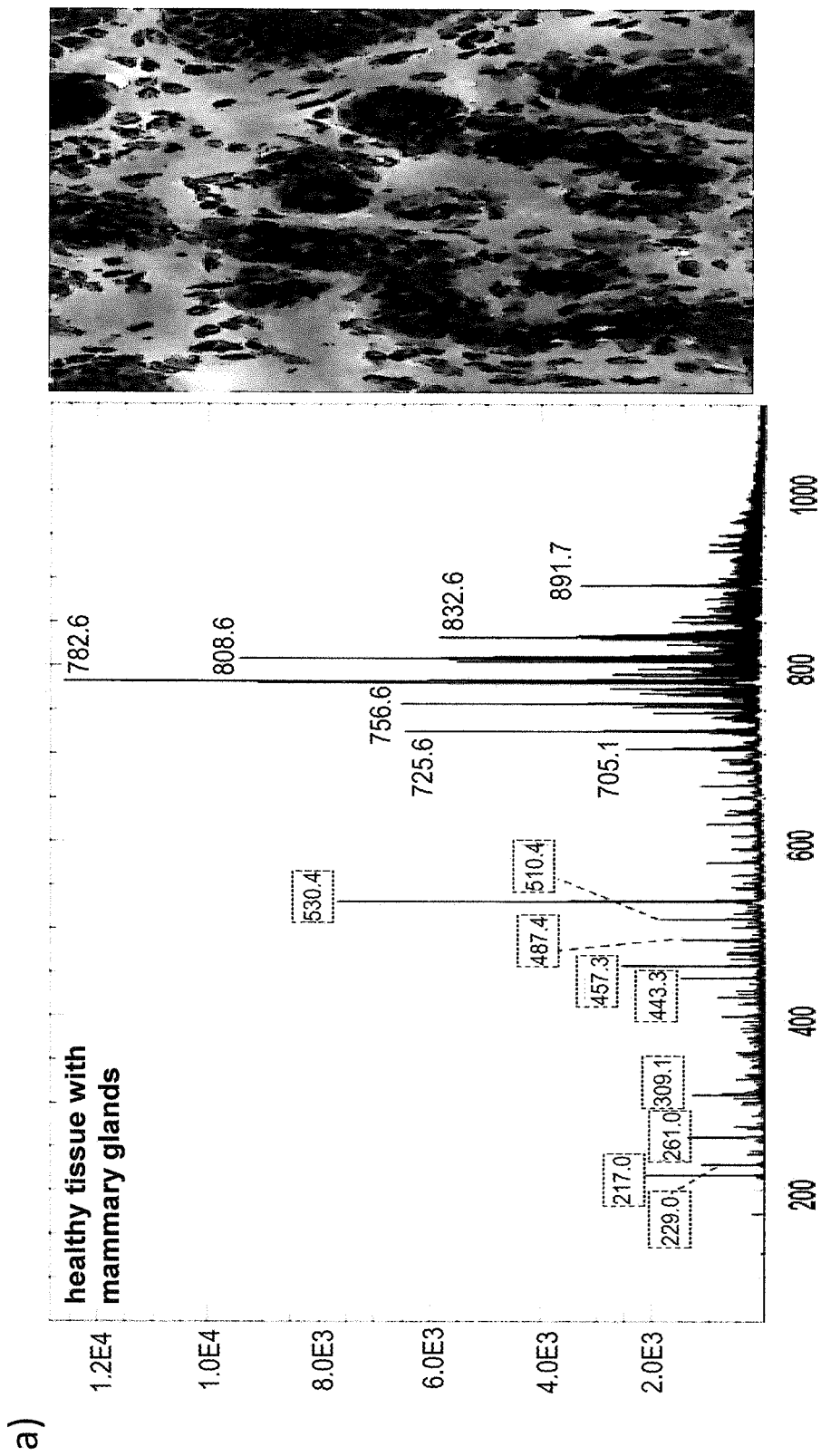
FIGS. 12(a-c). Profiled spectra in positive ion mode using DESI mass spectrometry from a) healthy tissue with mammary glands; b) healthy fatty tissue; c) tumor tissue. The histological images of representative tissue regions are shown on the right under 40X magnification.

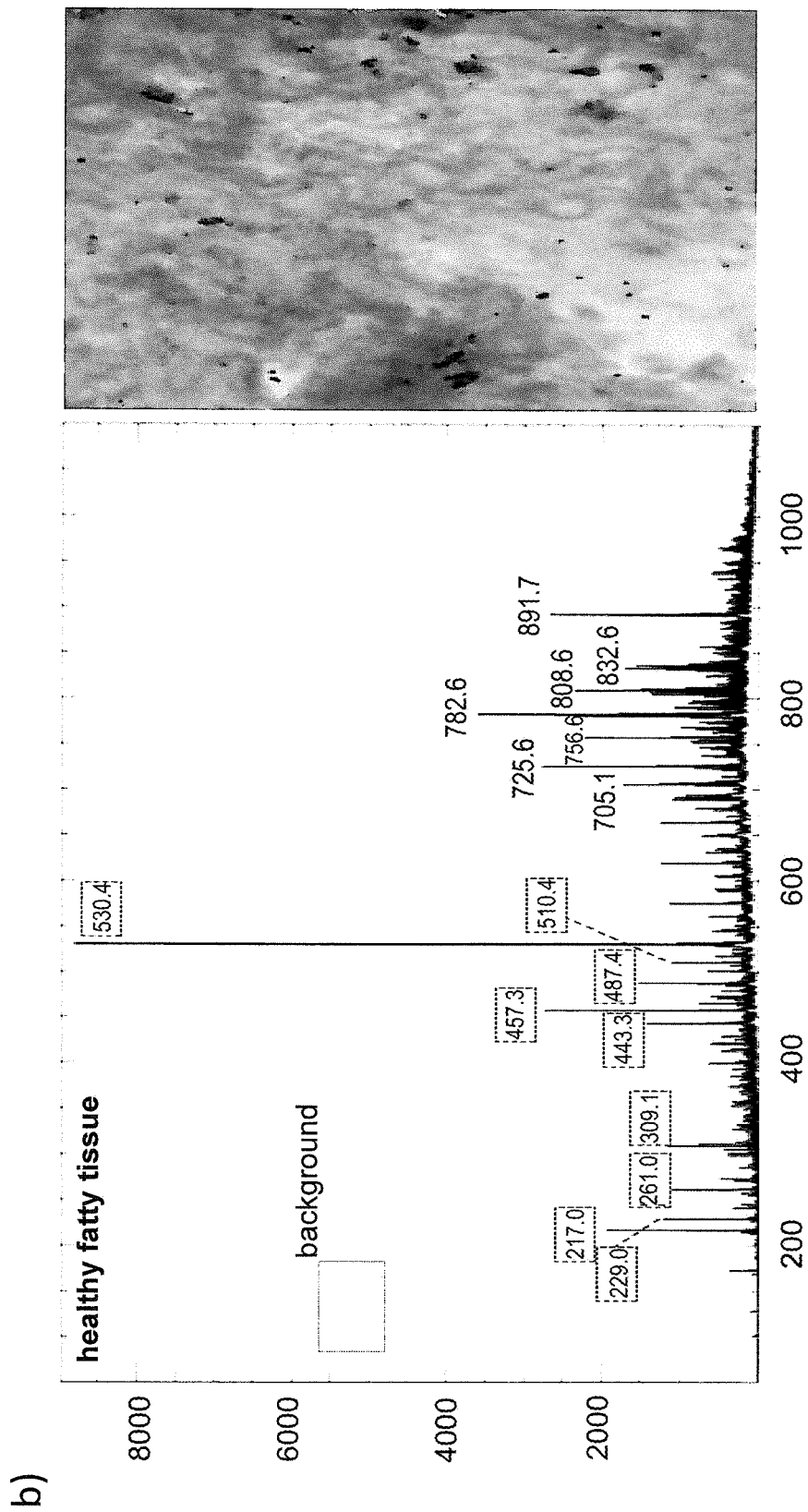
FIGS. 12(a-c) (continued). Profiled spectra in positive ion mode using DESI mass spectrometry from a) healthy tissue with mammary glands; b) healthy fatty tissue; c) tumor tissue. The histological images of representative tissue regions are shown on the right under 40X magnification.

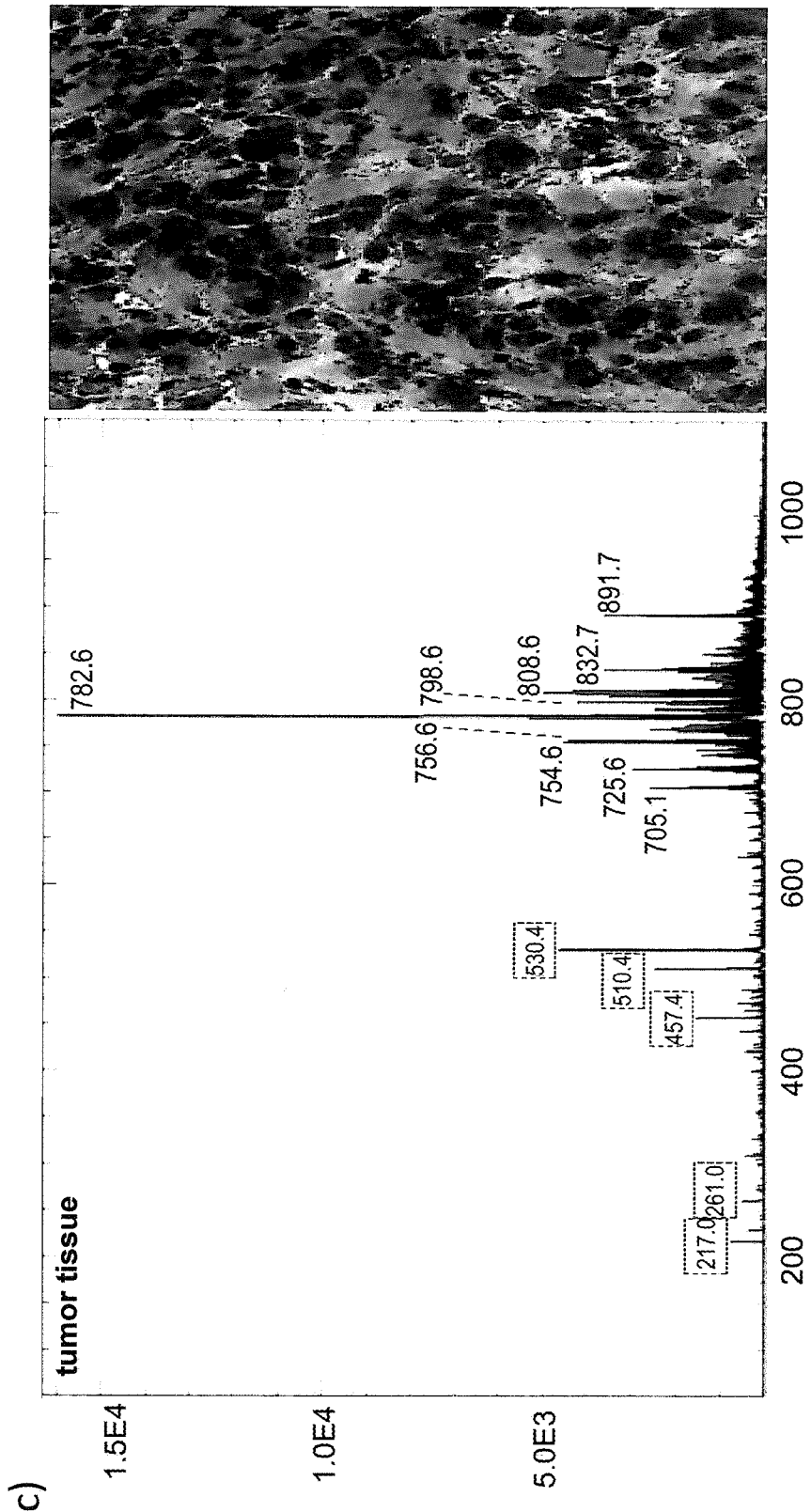
FIGS. 12(a-c) (continued) – Profiled spectra in positive ion mode using DESI mass spectrometry from a) healthy tissue with mammary glands; b) healthy fatty tissue; c) tumor tissue. The histological images of representative tissue regions are shown on the right under 40X magnification.

SYSTEM AND METHOD FOR ANALYZING TISSUE FOR THE PRESENCE OF CANCER USING BIO-MARKER PROFILES

CROSS-REFERENCE TO RELATED APPLICATIONS

The application represents the U.S. National Stage of International Application No. PCT/US2014/040501, filed Jun. 2, 2014 which is based on, claims priority to, and incorporates herein by reference in their entirety, U.S. Provisional Application Ser. No. 61/829,698, filed May 31, 2013, and entitled, "SYSTEM AND METHOD FOR ANALYZING TISSUE FOR THE PRESENCE OF CANCER USING BIO-MARKER PROFILES."

STATEMENT REGARDING FEDERALLY SPONSORED RESEARCH

This invention was made with government support under 5DP2OD007383-05 awarded by the National Institutes of Health. The government has certain rights in the invention.

BACKGROUND

The invention relates generally to intra-operative diagnostics of sample tissues. More specifically, the invention relates to the use of mass spectrometry for the detection of specific bio-markers.

Cancer presents many highly complex issues in clinical medicine. For example, consider just one of the many different and varied types of cancer, such as breast cancer. As a severely malignant and invasive tumor, breast cancer is a leading cause of death in cancerous women. Surgical removal of a cancerous tumor is usually the initial treatment of breast cancer, either by lumpectomy or mastectomy. Most women have a preference for the less invasive lumpectomy, for example, because of the cosmetic appearance. However, the accurate intra-operative determination of a tumor margin is challenging when planning and performing a breast-conserving surgery.

Normally, breast surgeons remove the tumor along with a few centimeters of surrounding healthy tissues on the basis of preoperative imaging using mammography, ultrasonography, or magnetic resonance imaging (MRI) to ensure the complete resection of cancer. Although accurate tumor size assessment may be available, the lack of real-time imaging in conjunction with surgical procedures relative to these techniques affects the surgery success rate and oftentimes leads to the need for further operations, giving the risk of local recurrence of breast cancer after lumpectomy and leading to a higher incidence of mastectomy. Therefore, the development of a technique allowing fast and in situ diagnosis and accurate characterization of a tumor margin boundary would facilitate a breast surgeon's decision making during lumpectomy.

The intra-operative application of MRI has been newly developed, especially in brain surgery. However, instead of providing real time imaging, this technique still requires the surgery to be interrupted. Ultrasonography has been applied intra-operatively in breast cancer excision, but it is unreliable in detecting nonpalpable tumor or ductal carcinoma in situ lesions. Positron emission tomography (PET), and near-infrared fluorescence (NIRF) optical imaging are two techniques that are being developed for intra-operative tumor assessment. However, the incorporation of radioactive or fluorescent labels presents a disadvantage not only to the patient but also to the operative personnel repeated exposure.

Thus, a need exists for an intra-operative diagnostic solution that provides a surgeon with more information about a tumor margin boundary.

BRIEF SUMMARY OF THE INVENTION

As discussed above, routine intra-operative distinction between tumor and normal breast tissue is currently not possible in breast conserving surgery. This limitation affects the success of breast cancer surgery, resulting in up to about forty percent (40%) of operations requiring more than one operative procedure.

Mass spectrometry imaging (MSI) has been applied to investigate the molecular distribution of proteins, lipids and metabolites without the use of labels. In particular, desorption electrospray ionization (DESI) allows direct tissue analysis with little or no sample preparation. Therefore, with the advantage of easy implementation, DESI mass spectrometry imaging (DESI-MSI) has great potential in the application of intra-operative tumor assessment.

The present invention overcomes the aforementioned drawbacks by providing a system and method for using DESI-MSI to correlate lipid distribution in two or three dimensions with tissue morphology, using this information, distinguishing cancerous from noncancerous tissues based on lipidomic information. The present invention provides a system and method that uses distinctive lipid profiles associated with different human cancers to make such determinations using DESI-MSI. Moreover, the present invention can use grades and subtypes of human brain tumors to discriminate using such techniques, along with delineating tumor margin in a manner well correlated with histopathological examination. Thus, the present invention uses a mass-spectrometry based methodology to distinguish cancerous from noncancerous tissue and delineate a tumor boundary according to lipidomic information obtained from DESI MSI. Such information can be utilized intra-operatively for rapid tumor margin determination in breast conserving surgery.

One aspect of the present invention provides a system and method for identification and differentiation of tumor versus healthy breast tissue. Discrimination between cancerous and adjacent normal tissue may be achieved on the basis of the spatial distributions and varying intensities of different lipid species. Several fatty acids, such as oleic acid (m/z 281), may be more abundant in harvested cancer specimens when compared to normal tissues. Cancer margins delineated by the molecular images from desorption electrospray ionization mass spectrometry imaging (DESI-MSI) are consistent with those obtained from histological staining.

In another aspect, the present invention provides an intra-operative solution for rapid detection of residual cancer tissue in a lumpectomy bed during breast conserving surgery.

In another aspect, the invention provides a method for intra-operative sample analysis that includes acquiring a tissue sample, preparing the tissue sample for mass spectrometry imaging, conducting a mass spectrometry imaging procedure on the tissue sample to produce an image, and analyzing the image to determine the presence or absence of a bio-marker.

In another aspect, the invention provides a mass spectrometry system that includes a sample receptacle configured to receive a tissue sample from a subject, a mass spectrometry apparatus configured to receive the tissue sample from the sample receptacle and analyze the tissue sample using a mass spectrometry process to determine a presence of a bio-marker indicating a presence of cancer in the tissue sample, and a report generator configured to deliver a report indicating a likelihood of cancer remaining in the subject.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

FIG. 1 is a summary of tissues samples used in exemplary experiments.

FIG. 2 is a detail of an exemplary bio marker.

FIG. 3 is a detail of another exemplary bio marker.

FIG. 4 is a detail of another exemplary bio marker.

FIG. 5 is a detail of another exemplary bio marker.

FIGS. 6(a-c) is a profiled spectra taken in a negative ion mode in accordance with the present invention using DESI-MSI.

FIGS. 7(a-e) is a series of images taken in accordance with the present invention using DESI-MSI.

FIGS. 8(a-d) is another series of images taken in accordance with the present invention using DESI MSI.

FIGS. 9(a-c) is an averaged and normalized spectra of ions taken in the negative ion mode in accordance with the present invention using DESI MSI on the samples of FIG. 1.

FIGS. 10(a-b) illustrate a principle component analysis (PCA) of cases 9 and 14 using the software suite ClinPro-Tools (Bruker Daltonics). In particular, FIG. 10a shows case 9 samples representing normal signatures such as contralateral breast, 5 cm and 2 cm away, clustered together, while the tumor edge and tumor samples derive from the normal cluster. Individual points each represent a spectrum (pixel) from the samples, and the samples harboring *tumor* derive from normal in a gradient suggesting an infiltrating edge or heterogenous composition of the tissue. FIG. 10b shows case 14 spectra from the *tumor* edge clustered between normal and cancerous sample. A combine analysis of both cases shows an overlap between *tumor* and *tumor* edge of both cases, and a clustering of 2 cm away, 5 cm away, and contralateral.

FIGS. 11(a-e) is another series of images taken in accordance with the present invention using DESI-MSI.

FIGS. 12(a-c) is another profiled spectra taken in the negative ion mode in accordance with the present invention using DESI-MSI.

Figure 13:
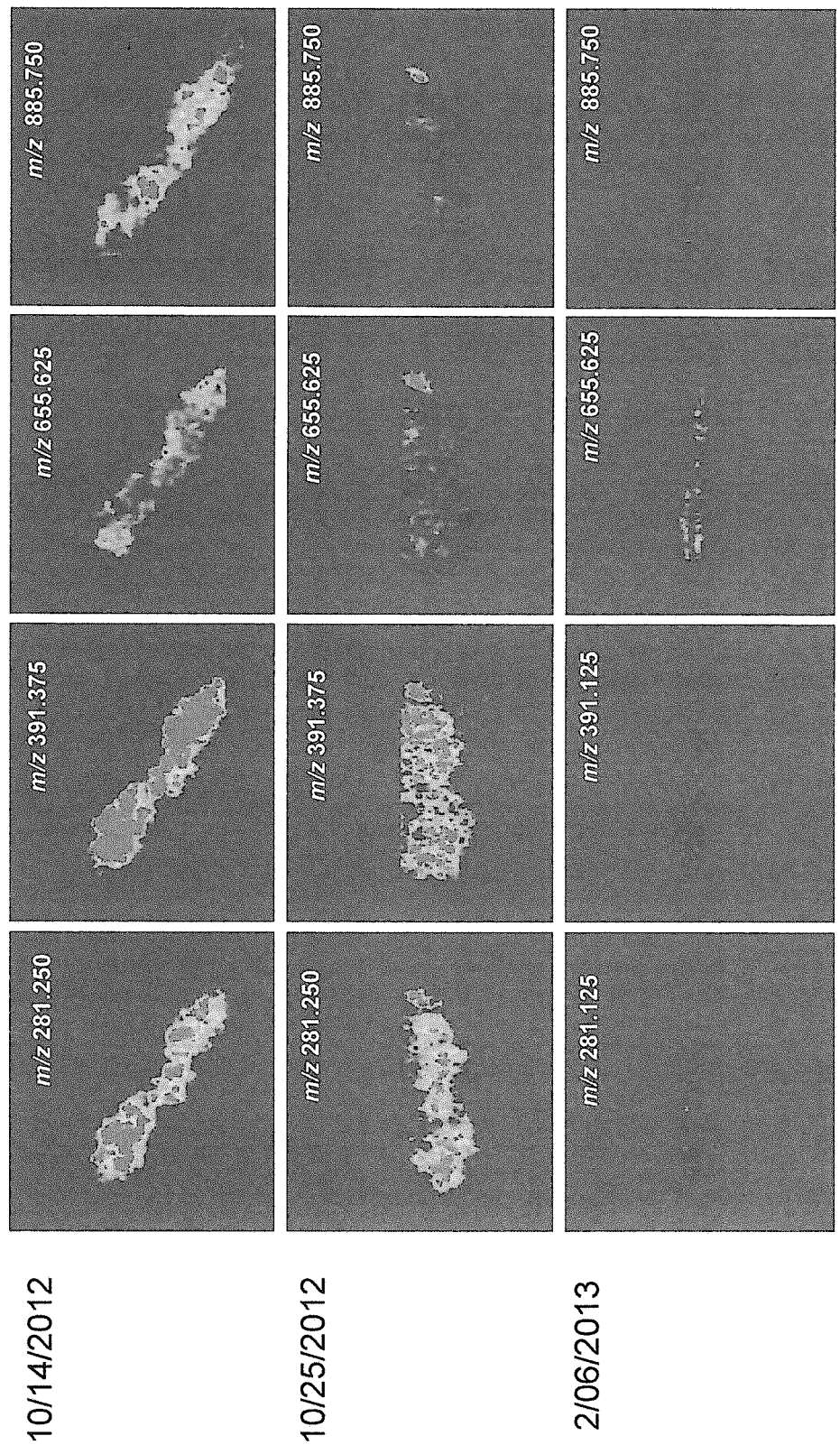
FIG. 13 is another series of images taken in accordance with the present invention using DESI-MSI.
Figure 13:
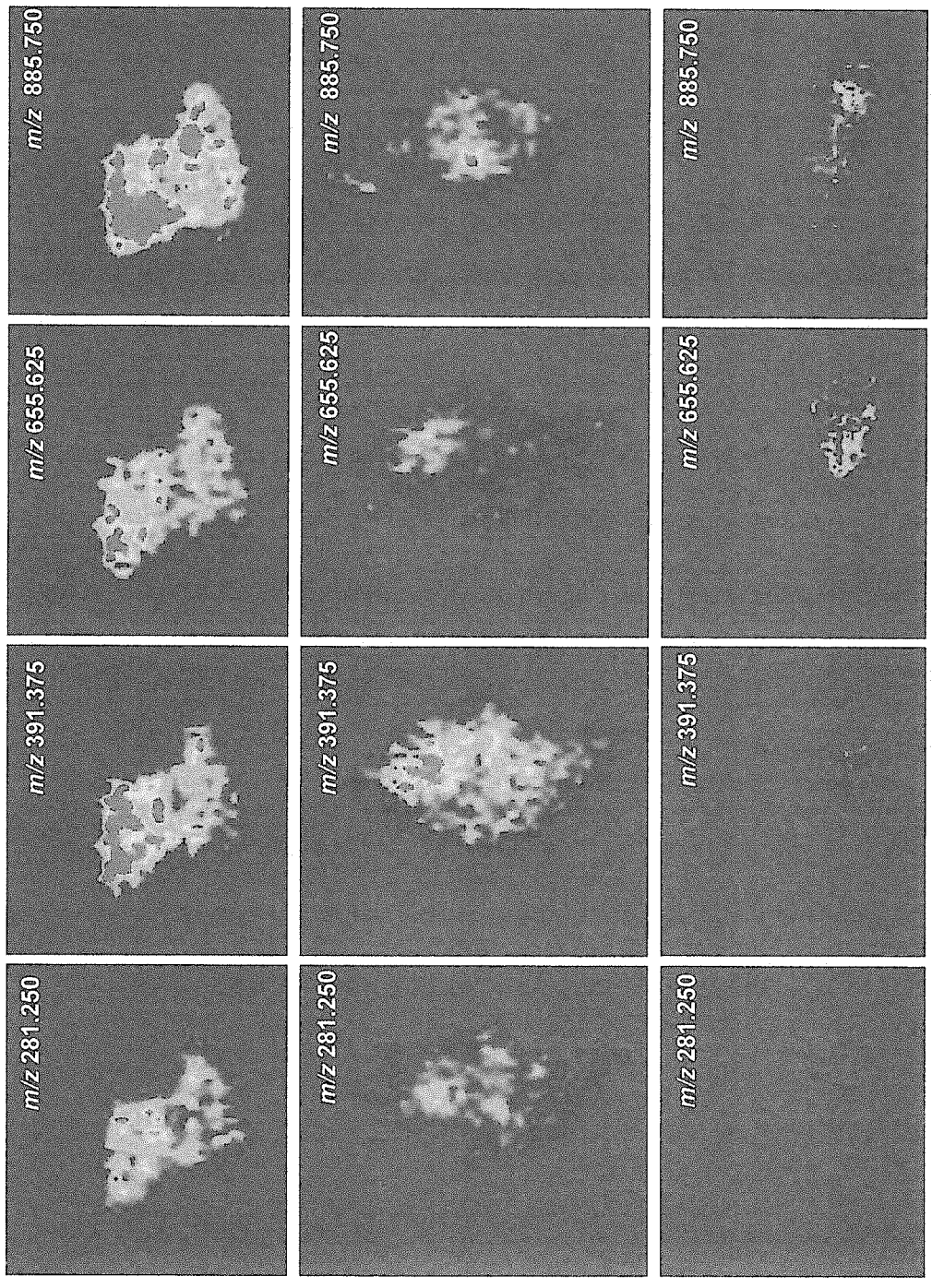

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

The following description of the invention is divided into three sections. The first section discusses various details an exemplary method methodology of sample acquisition and imaging in accordance with the present invention. The second section illustrates exemplary results of the use thereof. The third section discusses how various portions of the method work together toward the inventive system and method.

Methodology:

Tissues Sample Preparation:

During development of the invention, Applicants obtained sixty-one (61) cancerous breast samples removed via mastectomy from fourteen (14) research subjects from Brigham and Women Hospital. The samples (shown in FIG. 1) were collected at a *tumor* center, a *tumor* edge, 2 cm away from the *tumor* edge, 5 cm away from the *tumor* edge, and from a contralateral breast when available. The types of breast cancer were classified based on the status of three most important receptors: estrogen receptor (ER), progesterone receptor (PR) and human epidermal growth factor receptor 2 (Her2). Among the fourteen cases, nine of them have the *tumor* type ER positive, PR positive and Her2 negative (ER/PR+, Her2−), which is the most commonly found in breast cancer. As to the gender, one male was included.

Samples were flash frozen and stored in −80° C. freezer prior to analysis. The tissues were sectioned at 12 µm thickness using Microm HM550 crystat (Mikron Instrument Inc). 20 µm thickness was selected in several cases with fatty tissue. All the samples were mounted on regular glass slides. The slides were dried in a dessicator before analysis.

DESI Mass Spectrometry Imaging:

All the samples were analyzed using AmazonSpeed mass spectrometer (Bruker Daltonics, Mass.) connected with a commercial DESI source (Prosolia Inc., IN). The stage holding the glass slides mounted with tissue sections moved horizontally at the speed of 200 µm/s and vertically by 200 µm step to generate 2D image. The stage movement was controlled by OminiSpray 2D (Prosolia Inc., IN). A nondestructive solvent containing 50% acetonitrile and 50% dimethylformamide was used. A flow rate of 1 µL/min was selected for the solvent spray. The spectra were acquired within the mass range m/z 50-1100 with Bruker software Hystar (Bruker Daltonics, Mass.). In order to display 2D image, FireFly (Prosolia Inc., IN) was used to convert the data to be compatible with Biomap. All the images obtained from Biomap were displayed with the same intensity scale in each figure.

Histological Staining:

Standard hematoxylin and eosin staining (H&E Staining) was performed on the same tissue section after DESI MS imaging as well as serial sections to visualize tissue morphological information. Glass coverslips were used to cover slides with toluene in between as mounting medium. All the reagents used for H&E staining were purchased from Sigma (Sigma-Aldrich, St. Louis, Mo.). The optical tissue images were scanned using Axio Imager M1 microscope (Zeiss, Chester, Va.) at 40× magnification. The morphology of tissue sections was evaluated on the Mirax Digital Slide Desktop Server system.

Results:

Lipid Profiling in Breast Cancer Tissues Using DESI-MSI in Negative Ion Mode:

As discussed above, tissue samples from a total of fourteen research subjects with various ages were analyzed using DESI-MS imaging. All the samples were analyzed in a negative ion mode. The spectra were collected within the range of m/z 50-1100. Therefore, the negatively charged ions from lipids and metabolites were acquired. To validate day-to-day reproducibility, mouse brain sections were tested in exactly the same condition at the beginning of the day before acquiring breast cancer data.

The representative profiled spectra from breast cancerous and healthy tissue sections are shown in FIGS. 6(a-c) with corresponding optical images after histological staining. DESI-MS analysis followed by standard H&E staining was performed on the same tissue sections. The nondestructive spray solvent containing 50:50 ACN/DMF was used in the experiment and the tissue integrity was preserved after DESI-MS, allowing the subsequent histological analysis. The feasibility of evaluating these H&E stained tissues was approved by a breast pathologist. In healthy tissue from mammary glands and normal fatty tissue, similar lipid ion species and relative abundance (e.g. PS18:0/18:1 with m/z 788.7 and PI18:0/20:4 with m/z 885.7) were observed (FIGS. 6a and 6b), whereas the signals in fatty tissue were less intense. The dominant ions from healthy tissues were within the mass range m/z 700-1000. It can be concluded that these lipids came from noncancerous cells and higher intensities were obtained from mammary glands only because of the high cell density. However, distinct lipid species and intensities were observed, in the profiled spectrum from breast cancer tissue, especially in low mass region (FIG. 6c). Distinctive fatty acid ions were detected in low mass range <m/z 400 and lipids around m/z 600 were more abundant in cancerous tissues. In contrast, only background peaks were observed in low mass range <m/z 500 in healthy tissue in FIGS. 6a and 6b.

Based on the profiled spectra, significantly distinct lipids were detected from breast cancer and normal cells. Distinctive peak patterns in low mass region were observed in *tumor* tissue. However, the tissues from *tumor* edge, depending on cancer cell concentration, gave varying relative abundance in low mass range of the profiled spectra.

DESI-MSI of Breast Cancer Tissues in Negative Ion Mode:

DESI-MSI was performed on the breast cancer samples to display two-dimensional images correlating the lipid intensities with spatial distributions. Chemical information combining with tissue morphology is able to confirm the differentiation of *tumor* and healthy tissue based on molecular images from DESI-MSI.

FIGS. 7(a-e) includes the DESI-MSI images from samples of a *tumor* center, a *tumor* edge, 2 cm away and 5 cm away from the *tumor* edge, and a contralateral breast of research subject #9 respectively. Four ions, m/z 281.250 (oleic acid), m/z 391.375, m/z 655.625 and m/z 885.750 (PI18:0/20:4), were selected as representatives. All these images were plotted with the same color scale. The lipid PI18:0/20:4, present in both healthy and cancerous cells, was used as a control to state successful ion detection. Evidently, PI18:0/20:4 is more abundant in the areas with mammary glands and *tumor*. The DESI-MS images from healthy tissues (2 cm away, 5 cm away from *tumor* and contralateral side) were highly consistent with mammary gland distributions stained by H&E staining of the same sections. However, distinct images were observed for ions with m/z 281.250, m/z 391.375 and m/z 655.625. These lipids were very abundant in the *tumor* center, where there was high *tumor* cell density (FIG. 7a), whereas these lipids were absent or weak in healthy tissues (FIGS. 7c, 7d and 7e). Interestingly, in the tissue section from the *tumor* edge the *tumor* margin was significantly delineated by the ion images of m/z 281.250, m/z 391.375 and m/z 655.625, which agreed well with the one demonstrated by the histological staining of the same section. The ion with m/z 655.625 was still present although very weak in normal cells.

Another example from research subject #14 is shown in FIGS. 8(a-d). Similarly, the ions with m/z 281.250 and m/z 391.375 were abundant in the *tumor* center (FIG. 8a), but absent in healthy tissues from 2 cm away and 5 cm away from the *tumor* (FIGS. 7c and 7d). The ion with m/z 655.625 was less intense but still observed in normal tissues with similar distributions as mammary glands in normal tissues. Interestingly, the DESI MSI of these ions were distinct in the *tumor* edge. In contrast with the ion with m/z 655.625, m/z 281.250 and m/z 391.375 were abundant only on the edge of tissue.

Tumor and normal tissues were able to be distinguished unambiguously based on single molecular image of certain lipid obtained from DESI-MSI. Overall 12 out of 14 cases demonstrated striking difference for ion images with m/z 281.250 and m/z 391.375 between *tumor* and healthy tissues. The use of nondestructive solvent with 50/50 ACN/DMF allows the subsequent histopathological evaluation on the same section as the tissue integrity was retained. The tissues from the *tumor* edge revealed distinctive molecular images but consistent with the *tumor* cell distributions evaluated by breast pathologist, allowing the delineation of *tumor* margin. The results establish the possibility of incorporating DESI-MSI intra-operatively for rapid diagnosis of breast cancer tissue.

A typical spectrum to represent unique peaks only from *tumor* cells can be obtained by subtracting the ions coming from normal cells from the ions coming from *tumor* as shown in FIGS. 9(a-c). The average of 13 and 14 spectra from the *tumor* and normal tissues respectively are displayed in FIGS. 9a and 9b with the subtracted spectrum shown in FIG. 9c. The ion intensities were normalized before the subtraction. While the lipid abundance was decreased dramatically in the mass range >m/z 700 after subtraction with some even having negative intensity e.g. m/z 885.8, the representative peaks from *tumor* were significant in the subtracted spectrum, especially in low mass region. This distinctive subtracted spectrum can be used in the statistical analysis in the future to guide the intra-operative identification of *tumor* tissue.

Principle Component Analysis:

Although the *tumor* tissue can be differentiated from healthy tissue simply according to single molecular image from DESI-MSI, principle component analysis (PCA) was conducted for more accurate evaluation using ClinProTool. The statistical analysis of data from research subject #9 and #14 were shown in FIGS. 10a and 10b respectively. Separation of the spectra from the *tumor* and normal tissue was observed in both cases. In FIG. 10a, the spectra from *tumor* edge of research subject #9 were mostly clustered with spectra from *tumor*, whereas those from research subject #14 in FIG. 10b the *tumor* edge spectra were clustered between normal and cancerous sample. A combine analysis of both cases shows an overlap between *tumor* and *tumor* edge of both cases, and a clustering of 2 cm away, 5 cm away, and contralateral.

Abnormal Observation of Oleic Acid:

An interesting phenomenon was observed in research subject #5 that oleic acid signals (m/z 281.2) in normal tissues were increased dramatically (FIGS. 11c and 11d) compared with the *tumor* center and the *tumor* edge (FIGS. 11a and 11b), while the ions with m/z 391.375 and m/z 655.625 remained with low intensity. The dominance of oleic acid in the profiled spectrum of normal tissue is obviously visualized in FIG. 11e. Serial sections were analyzed repeatedly using DESI-MSI and similar results were obtained.

Lipid Analysis of Breast Cancer Tissues in Positive Ion Mode:

The tissue sections from normal and *tumor* samples were also analyzed using DESI-MSI in positive mode. The representative spectra are shown in FIGS. 12(a-c). The same lipid species were observed in both *tumor* and normal tissues, mostly PC and SM lipids. Similar to the negative ion mode, the healthy tissue with mammary glands gave more abundant signals compared to the normal fatty tissue (FIGS. 12a and 12b). However, in the profiled spectrum from the *tumor* tissue, the relative abundance of m/z 782.6 to other ions was dramatically changed (FIG. 12c). The ion images obtained by DESI-MSI failed to exhibit the discrimination between *tumor* and mammary glands in normal tissues with similar cell density. However, the incorporation of unique lipid relative abundance in the *tumor* is able to improve the confidence of detecting cancer tissue based on MS analysis.

Discussion:

A mass spectrometry based methodology is demonstrated here to distinguish breast cancerous and noncancerous tissue in order to potentially facilitate breast surgeon's decision making intra-operatively. Samples from 14 research subjects acquired at various locations of breast with *tumor* were investigated. The application of DESI-MSI enables the differentiation of the *tumor* from normal tissues and determination of a *tumor* boundary based on molecular images.

Compared with positive ion mode, the lipid spectra obtained from negative ion mode gives more unique information. In the profiled spectrum from negative ion mode, distinctive fatty acids and lipids were identified in breast cancer tissues. About 85% of the samples showed a significant increase of ion abundance in the low mass region (<m/z 700) in *tumor* samples, while most ions in high mass range (e.g. m/z 885.7) exist in normal cells as well. A "*tumor*" spectrum can be obtained by subtracting the ions coming from normal tissue, which represents the unique ions from cancer and facilitates *tumor* tissue diagnosis using mass spectrometry. In 2D images from DESI-MSI, the distinction of cancer and healthy tissue can be directly visualized. The *tumor* margin was able to be delineated even based on single molecular image validating the DESI-MS based diagnosis of breast cancer. Statistical analysis was performed to confirm the classification of *tumor* and normal tissues.

It is known that the lipids in breast samples degrade quickly during defrosting. In the exemplary experiments discussed above, although the samples were transferred carefully from −80° C. freezer to −20° C. crystat for sectioning, the dramatic decrease of lipid signals were observed in DESI-MSI when the tissues were resectioned. The comparison of the tissues from the same sample but sectioned and analyzed at different days is shown in FIG. 13. Obviously, the lipid ions were much less abundant on Feb. 6, 2013. Therefore, in order to obtain reliable lipid information, it is important to retain the samples fresh before analysis.

FIGS. 2-5 show details of a number of bio-markers that may be useful for identifying *tumor* margins or boundaries. These bio-markers were uncovered during Applicants' study of DESI-MSI analysis. Further, the following bio-markers were uncovered in the negative ion mode:

| MARKER | CHEMICAL FORMULA |
|---|---|
| m/z 89.1 | TBD |
| m/z 281.3 | C18H34O2 |
| m/z 303.3 | C20H32O2 |
| m/z 365.4 | C24H46O2 |
| m/z 391.4 | C26H48O2 |
| m/z 413.4 | . . . |
| m/z 445.4 | . . . |
| m/z 572.6 | . . . |
| m/z 626.8 | . . . |
| m/z 656.8 | . . . |
| m/z 682.8 | . . . |

The markers represented above and in FIGS. 2-5 are examples only. Other markers may exist and would be detected by the inventive system and method. In addition, all chemical formulas, names, identifications, and classifications are exemplary and form no boundary about the invention.

Figure 14:
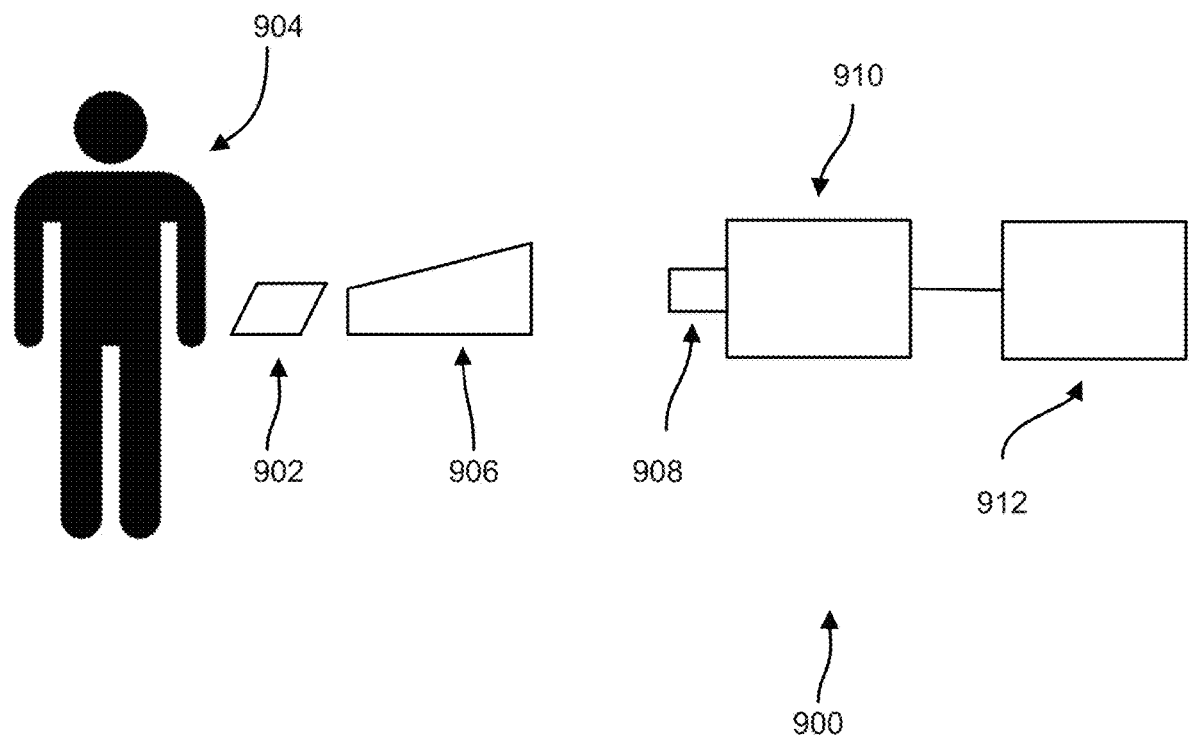
FIG. 14 is a schematic of a system in accordance with the present invention.

Specifically, turning to FIG. 14, a system 900 is provided in accordance with the present invention that is designed to analyze a sample 902 acquired from a subject 904, particularly during an operative procedure. The system 900 may be configured for use with a tool or probe 906 to assist or work in conjunction with other systems for providing the sample 902 to a sample receptacle 908 of the system 900. For example, it is contemplated that the system may be compatible with systems or method or include systems disclosed in co-pending U.S. patent application Ser. No. 13/059,524, which is incorporated herein by reference in its entirety. Once a sample is provided to the sample receptacle 908, the sample is processed by a mass-spectrometry system 910. The mass-spectrometry system 910 analyzes the tissue to determine a presence of a bio-marker indicating a presence of cancer in the tissue sample. The mass-spectrometry system 910 may be a desorption electrospray ionization apparatus. In any case, the mass-spectrometry system 910 is coupled to a report generator 912 that is configured to deliver a report indicating a likelihood of cancer remaining in the subject based on the analysis and, more particularly, the above-described bio-markers. The report generator 912 may include a printing system to print a physical report or may include a display to display a report, including figures and user-interface components, for example, such as described with respect to FIGS. 6-13 and those derived therefrom.

The invention has been described in connection with what are presently considered to be the most practical and preferred embodiments. However, the present invention has been presented by way of illustration and is not intended to be limited to the disclosed embodiments. Specifically, the above specific methods used are exemplary of the inventive concept and may be altered while still falling within the scope and spirit of the invention. Accordingly, those skilled in the art will realize that the invention is intended to encompass all modifications and alternative arrangements within the spirit and scope of the invention as set forth in the appended claims.

I claim:

1. A method for intra-operative sample analysis, the method including steps comprising:
   (a) preparing a breast tissue sample from a subject for mass spectrometry imaging;
   (b) imaging the breast tissue sample to produce a spectrographic report, the imaging of step (b) using a desorption electrospray ionization (DESI) mass spectrometry imaging (MSI) procedure in negative ion mode;
   (c) determining a presence of a lipid bio-marker in the breast tissue sample from the spectrographic report, including detecting ion peaks at m/z 89.1, m/z 365.4, m/z 391.4, m/z 413.4, m/z 445.4, m/z 572.6, m/z 626.8, m/z 656.8, and m/z 682.8 in the spectrographic report; and
   (d) generating a report indicating a likelihood of breast cancer in the subject based on step (c).

2. The method of claim 1, wherein the lipid bio-marker comprises a fatty acid.

3. The method of claim 2, wherein the fatty acid comprises oleic acid.

4. The method of claim 1, wherein the ion peaks are further detected at m/z 281.3 or m/z 303.3.

5. The method of claim 1, further comprising performing histological staining of the breast tissue sample.

* * * * *